US010064671B2

United States Patent
Sharkey et al.

(10) Patent No.: US 10,064,671 B2
(45) Date of Patent: Sep. 4, 2018

(54) INSTRUMENTS AND DEVICES FOR SUBCHONDRAL JOINT REPAIR

(75) Inventors: Peter F. Sharkey, Villanova, PA (US); Christopher D. Mandeen, West Chester, PA (US); Shaun B. Hanson, West Chester, PA (US); Jamie A. Carroll, Drexel Hill, PA (US)

(73) Assignee: ZIMMER KNEE CREATIONS, INC., Exton, PA (US)

( * ) Notice: Subject to any disclaimer, the term of this patent is extended or adjusted under 35 U.S.C. 154(b) by 546 days.

(21) Appl. No.: 13/491,958

(22) Filed: Jun. 8, 2012

(65) Prior Publication Data

US 2012/0316513 A1 Dec. 13, 2012

Related U.S. Application Data

(60) Provisional application No. 61/495,323, filed on Jun. 9, 2011.

(51) Int. Cl.
*A61B 17/88* (2006.01)
*A61F 2/46* (2006.01)
(Continued)

(52) U.S. Cl.
CPC ...... *A61B 17/8811* (2013.01); *A61B 17/3472* (2013.01); *A61B 17/7098* (2013.01);
(Continued)

(58) Field of Classification Search
CPC ........... A61B 17/8805; A61B 17/8808; A61B 17/8811; A61B 17/8816; A61B 17/8825;
(Continued)

(56) References Cited

U.S. PATENT DOCUMENTS 3,840,008 A * 10/1974 Noiles ................. A61M 5/3286
604/117
3,893,445 A * 7/1975 Hofsess ............... A61B 10/025
600/567
(Continued)

FOREIGN PATENT DOCUMENTS

CN 103841927 A 6/2014
EP 2717808 A2 4/2014
(Continued)

OTHER PUBLICATIONS

May 12, 2008 Riddle Memorial Hospital, Medial, PA 19063 Operative Report. Surgeon: Peter F Sharkey, M.D.; Right knee, medial tibial plateau; A cannulated bone biopsy needle was placed into the bone under fluoroscopic guidance; Implant used: Stryker Orthopedics Hydroset (Bone Substitute Material); Surgeon also expressed difficulty in injecting the bone substitute.
(Continued)

*Primary Examiner* — Matthew Lawson
*Assistant Examiner* — Amy Sipp
(74) *Attorney, Agent, or Firm* — Schwegman Lundberg & Woessner, P.A.

(57) ABSTRACT

Instruments and associated methods are disclosed for treating joints, and particularly bone tissue. In general, the embodiments relate to instruments and associated methods for the surgical treatment of a joint, and particularly to a subchondral bone defect at that joint region. More specifically, the embodiments relate to instruments that allow fast, easy, precise, and controllable subchondral delivery to, or removal of materials from, a bone joint being treated.

15 Claims, 17 Drawing Sheets

(51) Int. Cl.
- *A61F 2/28* (2006.01)
- *A61B 17/70* (2006.01)
- *A61B 17/34* (2006.01)
- *A61B 90/00* (2016.01)

(52) U.S. Cl.
CPC ...... *A61B 17/8808* (2013.01); *A61B 17/8819* (2013.01); *A61F 2/28* (2013.01); *A61F 2/4601* (2013.01); *A61B 2090/036* (2016.02); *A61B 2090/062* (2016.02); *A61B 2090/064* (2016.02); *A61F 2002/2839* (2013.01)

(58) Field of Classification Search
CPC ........ A61B 17/8802–17/8847; A61B 17/1604; A61B 17/34; A61B 17/864; A61B 17/863; A61B 17/8625; A61M 5/3134; A61M 5/3286; A61M 2205/192; A61M 25/06; A61M 25/0606; A61M 25/0612; A61M 25/0618; A61M 25/0625
USPC ..... 606/92–94, 184, 185; 604/171, 192, 198
See application file for complete search history.

(56) References Cited

U.S. PATENT DOCUMENTS

| | | | |
|---|---|---|---|
| 4,142,517 A * | 3/1979 | Contreras Guerrero de Stavropoulos | A61B 10/025 600/567 |
| 4,329,989 A * | 5/1982 | Dallons et al. | 604/192 |
| 4,790,828 A * | 12/1988 | Dombrowski | A61M 5/3275 604/110 |
| 5,092,461 A * | 3/1992 | Adam | 206/365 |
| 5,176,655 A * | 1/1993 | McCormick et al. | 604/198 |
| 5,250,031 A * | 10/1993 | Kaplan et al. | 604/110 |
| 5,279,591 A * | 1/1994 | Simon | 604/263 |
| 5,423,766 A * | 6/1995 | Di Cesare | 604/192 |
| 5,423,824 A * | 6/1995 | Akerfeldt | A61B 10/025 600/567 |
| 5,456,267 A * | 10/1995 | Stark | A61B 10/025 128/898 |
| 5,514,137 A | 5/1996 | Coutts | |
| 5,556,429 A | 9/1996 | Felt | |
| 5,584,818 A * | 12/1996 | Morrison | 604/197 |
| 5,713,872 A * | 2/1998 | Feuerborn et al. | 604/192 |
| 5,755,809 A | 5/1998 | Cohen | |
| 5,925,020 A * | 7/1999 | Nestell | 604/198 |
| 6,001,080 A * | 12/1999 | Kuracina et al. | 604/171 |
| 6,077,253 A * | 6/2000 | Cosme | 604/263 |
| 6,140,452 A | 10/2000 | Felt | |
| 6,159,185 A * | 12/2000 | Tanihata | G01N 30/18 600/576 |
| 6,210,376 B1 | 4/2001 | Grayson | |
| 6,235,043 B1 | 5/2001 | Reiley | |
| 6,241,734 B1 | 6/2001 | Scribner | |
| 6,248,110 B1 | 6/2001 | Reiley | |
| 6,280,420 B1 * | 8/2001 | Ferguson et al. | 604/198 |
| 6,306,177 B1 | 10/2001 | Felt | |
| 6,395,007 B1 | 5/2002 | Bhatnager | |
| 6,554,830 B1 * | 4/2003 | Chappius | A61B 17/3472 606/246 |
| 6,564,083 B2 | 5/2003 | Stevens | |
| 6,565,572 B2 * | 5/2003 | Chappius | 600/300 |
| 6,607,561 B2 | 8/2003 | Brannon | |
| 6,613,054 B2 | 9/2003 | Scribner | |
| 6,629,959 B2 * | 10/2003 | Kuracina et al. | 604/192 |
| 6,719,731 B2 * | 4/2004 | Parmigiani | 604/192 |
| 6,719,761 B1 | 4/2004 | Reiley | |
| 6,746,451 B2 | 6/2004 | Middleton | |
| 6,827,720 B2 | 12/2004 | Leali | |
| 6,863,899 B2 | 3/2005 | Koblish | |
| 6,887,246 B2 | 5/2005 | Bhatnager | |
| 6,918,891 B2 * | 7/2005 | Bressler et al. | 604/198 |
| 7,153,307 B2 | 12/2006 | Scribner | |
| 7,261,720 B2 | 8/2007 | Stevens | |
| 7,361,159 B2 * | 4/2008 | Fiser et al. | 604/192 |
| 7,708,742 B2 | 5/2010 | Scribner | |
| 7,771,431 B2 | 8/2010 | Scribner | |
| 7,811,290 B2 | 10/2010 | Rabiner | |
| 8,062,364 B1 | 11/2011 | Sharkey et al. | |
| 8,152,813 B2 | 4/2012 | Osorio | |
| 8,168,692 B2 | 5/2012 | Wenz | |
| 8,690,930 B2 * | 4/2014 | Biedermann | A61B 17/7037 606/304 |
| 8,961,553 B2 * | 2/2015 | Hollowell et al. | 606/192 |
| 8,968,252 B2 * | 3/2015 | White et al. | 604/174 |
| 2001/0021852 A1 * | 9/2001 | Chappius | A61B 17/3472 600/300 |
| 2001/0039401 A1 * | 11/2001 | Ferguson et al. | 604/198 |
| 2002/0004650 A1 * | 1/2002 | Kuracina et al. | 604/198 |
| 2003/0028171 A1 * | 2/2003 | DeHarde et al. | 604/507 |
| 2003/0138473 A1 | 7/2003 | Koblish | |
| 2004/0111057 A1 * | 6/2004 | Wilkinson | 604/110 |
| 2004/0122431 A1 * | 6/2004 | Biedermann | A61B 17/864 606/62 |
| 2004/0167477 A1 * | 8/2004 | Wilkinson et al. | 604/263 |
| 2005/0015054 A1 * | 1/2005 | Chen | 604/192 |
| 2005/0107748 A1 * | 5/2005 | Thorne et al. | 604/263 |
| 2005/0107800 A1 * | 5/2005 | Frankel | A61B 17/1655 606/92 |
| 2005/0119219 A1 | 6/2005 | Bellini | |
| 2006/0064164 A1 | 3/2006 | Theien | |
| 2007/0142842 A1 * | 6/2007 | Krueger | A61B 17/8811 606/92 |
| 2007/0185510 A1 * | 8/2007 | Tran | 606/167 |
| 2007/0233123 A1 * | 10/2007 | Ahmad | A61B 17/863 606/307 |
| 2008/0097304 A1 * | 4/2008 | Thorne | 604/110 |
| 2008/0249530 A1 * | 10/2008 | Truckai | A61B 17/8822 606/94 |
| 2009/0131967 A1 * | 5/2009 | Hollis et al. | 606/185 |
| 2009/0198243 A1 * | 8/2009 | Melsheimer | A61B 17/8811 606/93 |
| 2009/0259201 A1 * | 10/2009 | Hwang et al. | 604/263 |
| 2010/0076503 A1 | 3/2010 | Beyar | |
| 2010/0179549 A1 | 7/2010 | Keller | |
| 2010/0286616 A1 * | 11/2010 | Baroud | 604/164.11 |
| 2011/0004256 A1 * | 1/2011 | Biedermann et al. | 606/301 |
| 2011/0060373 A1 * | 3/2011 | Russell et al. | 606/304 |
| 2011/0087167 A1 * | 4/2011 | Albrecht | A61B 17/3421 604/164.04 |
| 2011/0125156 A1 | 5/2011 | Sharkey et al. | |
| 2011/0125157 A1 | 5/2011 | Sharkey et al. | |
| 2011/0125264 A1 | 5/2011 | Bagga et al. | |
| 2011/0125265 A1 * | 5/2011 | Bagga | A61B 17/68 623/16.11 |
| 2011/0125272 A1 | 5/2011 | Bagga et al. | |
| 2011/0202065 A1 * | 8/2011 | Takizawa et al. | 606/94 |
| 2012/0053639 A1 * | 3/2012 | Grant | A61B 17/864 606/301 |
| 2012/0197311 A1 * | 8/2012 | Kirschman | 606/304 |
| 2012/0215247 A1 * | 8/2012 | Albrecht | A61B 17/3421 606/185 |
| 2012/0330320 A1 * | 12/2012 | Takizawa et al. | 606/94 |
| 2013/0110120 A1 * | 5/2013 | Baroud et al. | 606/102 |
| 2014/0336687 A1 * | 11/2014 | Iwase et al. | 606/185 |
| 2015/0030684 A1 * | 1/2015 | Pomrink et al. | 424/493 |
| 2015/0157370 A1 * | 6/2015 | Gross | 604/506 |

FOREIGN PATENT DOCUMENTS

| | | |
|---|---|---|
| WO | 1990/04364 A1 | 5/1990 |
| WO | 2003/011154 A2 | 2/2003 |
| WO | 2011/054122 A1 | 5/2011 |

OTHER PUBLICATIONS

Oct. 27, 2008 SPU Operative Report. Surgeon: Steven B Cohen, M.D.; An Anterior Cruciate Ligament (ACL) portal-creation device was repurposed for this surgery; The tibial probe was placed on the medial femoral condyle, with the tunnel guide secured proximally

(56) References Cited

OTHER PUBLICATIONS on the thigh; the surgeon expressed difficulty in positioning and stabilizing the guide; A cannulated pin was placed through the tunnel guide and placed distally into the medial femoral condyle; No implant was injected into the bone.
Nov. 10, 2008 SPU Operative Report. Surgeon: Steven B Cohen, M.D.; Treatment of the central medial tibial plateau; A guide pin was inserted into the medial tibial plateau; An endo button drill bit was used to expand the drill hole; One cubic centimeter (cc) of cement was inserted into the bone; A second drill hole was made from below, and a second cc was inserted into the bone.
International Search Report and Written Opinion dated Jan. 10, 2013 in corresponding International Application No. PCT/US2012/041534.
Republication of International Search Report dated Jan. 10, 2013 in corresponding International Application No. PCT/US2012/041534.
"Canadian Application Serial No. 2,838,816, Office Action dated Sep. 24, 2014", 1 pg.
"Canadian Application Serial No. 2,838,816, Response dated Oct. 24, 2014 to Office Action dated Sep. 24, 2014", 2 pgs.
"Australian Application Serial No. 2012267730, First Examiner Report dated Dec. 4, 2015", 3 pgs.
"Canadian Application Serial No. 2,838,816, Office Action dated Jun. 14, 2016", 3 pgs.
"Chinese Application Serial No. 201280038876.4, Office Action dated Jan. 28, 2016", 6 pgs.
"Chinese Application Serial No. 201280038876.4, Office Action dated Jun. 25, 2015", w/ English Translation, 12 pgs.
"Chinese Application Serial No. 201280038876.4, Response dated Apr. 11, 2016 to Office Action dated Jan. 28, 2016", with English translation of claims, 9 pgs.
"Chinese Application Serial No. 201280038876.4, Response dated Nov. 4, 2015 to Office Action dated Jun. 25, 2015", with English translation of claims, 13 pgs.
"Australian Application Serial No. 2012267730, Office Action dated Oct. 13, 2016", 4 pgs.
"Australian Application Serial No. 2012267730, Response dated Sep. 15, 2016 to First Examiner Report dated Dec. 4, 2015", 15 pgs.
"Australian Application Serial No. 2012267730, Response dated Nov. 22, 2016 to Office Action dated Oct. 13, 2016", 15 pgs.
"Canadian Application Serial No. 2,838,816, Response dated Oct. 20, 2016 to Office Action dated Jun. 14, 2016", 16 pgs.
"Chinese Application Serial No. 201280038876.4, Office Action dated Jul. 19, 2016", (English Translation), 9 pgs.
"Chinese Application Serial No. 201280038876.4, Response dated Oct. 8, 2016 to Office Action dated Jul. 19, 2016", W/ English Translation of Claims, 9 pgs.
"Chinese Application Serial No. 201280038876.4, Office Action dated Feb. 10, 2017", (W/ English Translation), 14 pgs.
"Chinese Application Serial No. 201280038876.4, Response dated Apr. 21, 2017 to Office Action dated Feb. 10, 2017", (W/ English Translation), 14 pgs.
"European Application Serial No. 12727755.6, Communication Pursuant to Article 94(3) EPC dated Mar. 2, 2018", 6 pgs.

\* cited by examiner

INSTRUMENTS AND DEVICES FOR SUBCHONDRAL JOINT REPAIR

CROSS-REFERENCE TO RELATED APPLICATIONS

This application claims priority to U.S. Provisional No. 61/495,323 filed Jun. 9, 2011 and entitled "Instruments and Devices for Subchondral Joint Repair," the content of which is incorporated by reference in its entirety.

FIELD

The present invention relates to instruments and devices for the surgical treatment of joints, and more particularly to instruments and devices for the subchondral repair and treatment of bone tissue at these joints, and associated methods of use.

BACKGROUND

Human joints, in particular the knee, hip and spine, are susceptible to degeneration from disease, trauma, and long-term repetitive use that eventually lead to pain. Knee pain, for example, is the impetus for a wide majority of medical treatments and associated medical costs. The most popular theory arising from the medical community is that knee pain results from bone-on-bone contact or inadequate cartilage cushioning. These conditions are believed to frequently result from the progression of osteoarthritis, which is measured in terms of narrowing of the joint space. Therefore, the severity of osteoarthritis is believed to be an indicator or precursor to joint pain. Most surgeons and medical practitioners thus base their treatments for pain relief on this theory. For example, the typical treatment is to administer pain medication, or more drastically, to perform some type of joint resurfacing or joint replacement surgery.

However, the severity of osteoarthritis, especially in joints such as the knee and ankle, has been found to correlate poorly with the incidence and magnitude of knee pain. Because of this, surgeons and medical practitioners have struggled to deliver consistent, reliable pain relief to patients especially if preservation of the joint is desired.

Whether by external physical force, disease, or the natural aging process, structural damage to bone can cause injury, trauma, degeneration or erosion of otherwise healthy tissue. The resultant damage can be characterized as a bone defect that can take the form of a fissure, fracture, microfracture, lesion, edema, tumor, or sclerotic hardening, for example. Particularly in joints, the damage may not be limited to a bone defect, and may also include cartilage loss (especially articular cartilage), tendon damage, and inflammation in the surrounding area.

Patients most often seek treatment because of pain and deterioration of quality of life attributed to the osteoarthritis. The goal of surgical and non-surgical treatments for osteoarthritis is to reduce or eliminate pain and restore joint function. Both non-surgical and surgical treatments are currently available for joint repair.

Non-surgical treatments include weight loss (for the overweight patient), activity modification (low impact exercise), quadriceps strengthening, patellar taping, analgesic and anti-inflammatory medications, and with corticosteroid and/or viscosupplements. Typically, non-surgical treatments, usually involving pharmacological intervention such as the administration of non-steroidal anti-inflammatory drugs or injection of hyaluronic acid-based products, are initially administered to patients experiencing relatively less severe pain or joint complications. However, when non-surgical treatments prove ineffective, or for patients with severe pain or bone injury, surgical intervention is often necessary.

Surgical options include arthroscopic partial meniscectomy and loose body removal. Most surgical treatments conventionally employ mechanical fixation devices such as screws, plates, staples, rods, sutures, and the like are commonly used to repair damaged bone. These fixation devices can be implanted at, or around, the damaged region to stabilize or immobilize the weakened area, in order to promote healing and provide support. Injectable or fillable hardening materials such as bone cements, bone void fillers, or bone substitute materials are also commonly used to stabilize bone defects.

High tibial osteotomy (HTO) or total knee arthroplasty (TKA) is often recommended for patients with severe pain associated with osteoarthritis, especially when other non-invasive options have failed. Both procedures have been shown to be effective in treating knee pain associated with osteoarthritis.

However, patients only elect HTO or TKA with reluctance. Both HTO and TKA are major surgical interventions and may be associated with severe complications. HTO is a painful procedure that may require a long recovery. TKA patients often also report the replaced knee lacks a "natural feel" and have functional limitations. Moreover, both HTO and TKA have limited durability. Accordingly, it would be desirable to provide a medical procedure that addresses the pain associated with osteoarthritis and provides an alternative to a HTO or TKA procedure.

One of the difficulties of currently available surgical access devices and insertion tools is the ability to target a specific area of the bone to be treated, in a fast, accurate, easy and controlled manner. Presently, in order to treat or repair a bone defect at a joint, the surgeon often has to take multiple steps using multiple surgical tools in order to access, locate, and treat the target defect site. Even so, the surgeon does not have a reliable instrument or system that would allow him to easily and quickly target an area such as the subchondral region of a joint, and either deliver or remove material to that target region. In order to perform repeated or multiple procedures in the same defect location with the currently available tools, additional and unnecessary time in the operating room would be required, as well as an increased risk for complications since numerous instruments and maneuvers are at play.

Accordingly, it is desirable to provide instruments that allow fast, easy, and controllable surgical access to the target site, or the bone defect, to be treated. It is further desirable to provide instruments that enable the user to easily and quickly deliver or remove material at the target site for treatment.

SUMMARY

The present disclosure provides instruments and associated methods for the surgical repair and treatment of bone tissue, particularly of bone tissue at joints. More specifically, the present disclosure provides instruments that allow fast, easy, precise, and controllable delivery or removal of materials subchondrally to a bone joint being treated.

In one embodiment, a delivery instrument is provided. The instrument may take the form of an injection needle. The injection needle may be configured to deliver material to a subchondral area of a bone joint to be treated. The injection needle may include a sharp tip, elongate shaft, and tool attachment end. In use, the injection needle may be threaded into the bone to be treated. The injection needle may be used with a stabilization instrument. The tool attachment end may be threaded for threaded connection to other instruments.

In another embodiment, a delivery instrument is provided. The instrument may be an injection needle configured to deliver material to a subchondral area of a bone joint to be treated. The injection needle may comprise a sharp tip, a tool attachment end, and an elongate shaft extending therebetween. The needle may be partially or wholly cannulated. It may also be fenestrated with helical grooves or spiral cutouts inside of which can reside injection ports or holes. These cutouts may serve as surface features that enable the injection needle to be threaded into bone tissue while the holes may allow the delivery of a material to the subchondral area of the bone. The cutouts may also direct or guide the flow of material out of the holes. Optionally, threads may be provided. The threads allow the needle to be threaded into the bone tissue during use.

In still another embodiment, a delivery instrument in the form of a semi-cannulated pin is provided. The semi-cannulated pin can be drilled into bone to deliver material. The pin may have etchings or indicia along the shaft that indicate depth or distance from the tip or relative distance to another marker. The pin may also have a marker, such as a visual or tactile marker, that indicates directionality. A secondary pin may also be placed inside the first pin and rotated to control the opening and closing of the hole or fenestration, and thereby the delivery of material out of the system.

In yet another embodiment, a delivery system is provided. The system may comprise a fenestrated cannula attached to a handle. The system may further include a stabilizer. The stabilizer may include a pin configured to slide into the cannula to stabilize it as it is being inserted into the subchondral region of the bone. After insertion, an injectable material may be deployed through the cannula. The pin may be driven down into the cannula forcing the material into the bone. The cannula may also be retracted so that the pin would force more material into the bone, with the injection rate being proportional to the retraction rate.

In still yet another embodiment, a delivery instrument is provided. The instrument may comprise a tip, an elongate shaft, a device attachment end, and a removable and slidable sleeve. The instrument may attach to a fenestrated cannula at the tip, while the device attachment end may attach to an injection system. The sleeve may comprise a split ring attached to a tether that connects to a band around the device attachment end. The sleeve is configured to slide over the elongate shaft of the instrument and the cannula, covering the fenestrations of the cannula.

In even still another embodiment, a gauge is provided. The gauge may be used with the cannulas or pins to provide volumetric and pressure readings while also a mechanical assist. The gauge allows the user even greater control over the amount of material injected into the bone as well as the volume and pressure of the material.

In another embodiment, two or more fenestrated cannulas can be used to allow both injection and removal of material from a bone to be treated. A bone plug may be provided to prevent injected material from exiting through the cannula at its tip instead of through the sides via the fenestrations. The plug may also be used to plug up any access holes created during the surgery.

In still another embodiment, a bone restricter or plug may be provided to restrict the flow of materials. The plug may be delivered into the subchondral space and allowed to expand or at the same time or before the material is injected. The plug may be provided to prevent injected material from exiting through the cannula at its tip instead of through the sides via the fenestrations.

In yet another embodiment, a fenestrated cannula may be provided with a one-way valve. The valve may allow the passage of a pin or wire, while restricting any backflow of material or bone substance.

In another embodiment, highly porous implants are provided. These implants may be housed internally within the cannula or other delivery instrument. The pores allow for the flow of material out of the cannula but also redirect or induce dispersion of the material during injection.

In still another embodiment, an injection material delivery system is provided. The system may comprise two components: an outer cannula with an open tip and an inner rod configured to slide inside the outer cannula, the inner rod having a closed end. Each of the outer cannula and inner rod have openings that can be aligned together to open the orifices, or misaligned to close the orifices. A locking mechanism can be provided to maintain the two components together. The system can be used with a plunger that is configured to be inserted through the outer cannula after the inner rod has been removed. A plug, such as for instance an allograft plug, may be used with the system to further prevent backflow of material out of the bone to be treated.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

DESCRIPTION OF THE EMBODIMENTS

Figure 1:
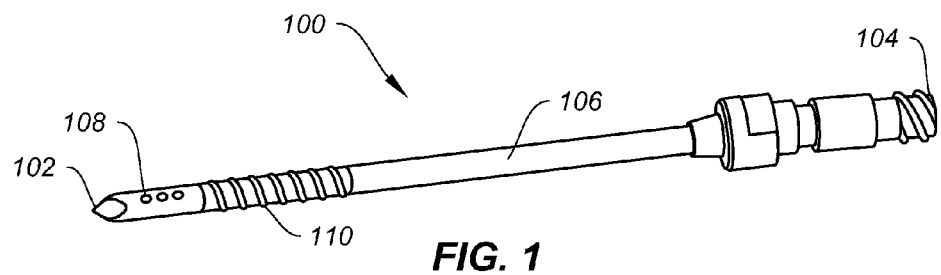
FIG. 1 shows a perspective view of an injection needle of the present disclosure.

The present disclosure provides methodologies, devices and instruments for diagnosing and treating joint pain to restore natural joint function and preserving, as much as possible, the joint's articular and cartilage surface. Treatments through the joint that violate the articular and cartilage surface often weaken the bone and have unpredictable results. Rather than focusing on treatment of pain through the joint, alternative treatments that diagnose and treat pain at its source in the subchondral region of a bone of a joint to relieve the pain are provided. Pain associated with joints, especially osteoarthritic joints, can be correlated to bone defects or changes at the subchondral level rather than, for example, the severity of osteoarthritic progression or defects at the articular surface level. In particular, bone defects, such as bone marrow lesions, edema, fissures, fractures, hardened bone, etc. near the joint surface lead to a mechanical disadvantage and abnormal stress distribution in the periarticular bone, which may cause inflammation and generate pain. By altering the makeup of the periarticular bone (which may or may not be sclerotic) in relation to the surrounding region, it is possible to change the structural integrity of the affected bone and restore normal healing function, thus leading to a resolution of the inflammation surrounding the defect.

Treatment of the bone by mechanical and biological means to restore the normal physiologic stress distribution, and restore the healing balance of the bone tissue at the subchondral level, is a more effect way of treating pain than conventional techniques. That is, treatment can be effectively achieved by mechanically strengthening or stabilizing the defect, and biologically initiating or stimulating a healing response to the defect. Methods, devices, and systems for a subchondral procedure that achieve these goals are disclosed in co-owned U.S. Pat. No. 8,062,364 entitled "OSTEOARTHRITIS TREATMENT AND DEVICE" as well as in co-owned and co-pending U.S. Patent Application Publication Nos. 2011/0125156 entitled "METHOD FOR TREATING JOINT PAIN AND ASSOCIATED INSTRUMENTS" and 2011/0125157 entitled "SUBCHONDRAL TREATMENT OF JOINT PAIN," both of which were filed on Nov. 19, 2010, the contents of which are incorporated by reference in their entirety. This subchondral procedure, and its associated devices, instruments, etc. are also marketed under the registered trademark name of SUBCHONDROPLASTY™. The SUBCHONDROPLASTY™ procedure is a response to a desire for an alternative to patients facing partial or total knee replacement.

In general, the SUBCHONDROPLASTY™ or SCP™ technique is intended to both strengthen the bone and stimulate the bone. In SCP™, bone fractures or non-unions are stabilized, integrated or healed, which results in reduction of a bone defect, such as a bone marrow lesion or edema. In addition, SCP™ restores or alters the distribution of forces in a joint to thereby relieve pain. SCP™ can be performed arthroscopically or percutaneously to treat pain by stabilizing chronic stress fracture, resolving any chronic bone marrow lesion or edema, and preserving, as much as possible, the articular surfaces of the joint. SUBCHONDROPLASTY™ generally comprises evaluating a joint, for example, by taking an image of the joint, detecting the presence of one or more subchondral defects, diagnosing, which of these subchondral defects is the source of pain, and determining an extent of treatment for the subchondral defect. The technique is particularly suited for treating chronic defects or injuries, where the patient's natural healing response has not resolved the defect. It should be noted, however, that the technique is equally applicable to treatment of defects in the subchondral region of bone where the defect is due to an acute injury or from other violations. Several exemplary treatment modalities for SCP™ for the different extents of treatment needed can be employed. Accordingly, a medical practitioner may elect to use the techniques and devices described herein to subchondrally treat any number of bone defects, as he deems appropriate.

Detection and identification of the relevant bone marrow lesion or bone marrow edema (BML or BME) can be achieved by imaging, e.g., magnetic resonance imaging (MRI), X-ray, bone scans, manual palpation, chemical or biological assay, and the like. A T1-weighted MRI can be used to detect sclerotic bone, for example. Another example is that a T2-weighted MRI can be used to detect lesions, edemas, and cysts. X-ray imaging may be suitable for early-stage as well as end-stage arthritis. From the imaging, certain defects may be identified as the source of pain. In general, defects that are associated with chronic injury and chronic deficit of healing are differentiated from defects that result, e.g., from diminished bone density. SCP™ treatments are appropriate for a BML or BME that may be characterized as a bone defect that is chronically unable to heal (or remodel) itself, which may cause a non-union of the bone, stress or insufficiency fractures, and perceptible pain. Factors considered may include, among other things, the nature of the defect, size of the defect, location of the defect, etc. For example, bone defects at the edge near the articular surface of periphery of a joint may be often considered eligible for treatment due to edge-loading effects as well as the likelihood of bone hardening at these locations. A bone defect caused by an acute injury would generally be able to heal itself through the patient's own natural healing process. However, in such situations where the bone defect is due to an acute injury and either the defect does not heal on its own, or the medical practitioner decides that the present technique is appropriate, SCP™ treatment can be administered on acute stress fractures, BML or BME, or other subchondral defects, as previously mentioned.

The SCP™ treatment may continue after surgery. In particular, the patient may be monitored for a change in pain scores, or positive change in function. For example, patients are also checked to see when they are able to perform full weight-bearing activity and when they can return to normal activity. Of note, the SCP™ procedure can be revised and thus allows for optional further treatment in the event that a patient requires or desires a joint replacement or other type of procedure. The procedure does not exclude a future joint repair or replacement treatment to be applied, and thus may also be performed in conjunction with other procedures, such as cartilage resurfacing, regeneration or replacement, if desired. In those instances where additional treatment is desired, the SCP™ treated area may remain undisturbed while the additional treatment is performed, such as where cartilage resurfacing is desired. Alternatively, the SCP™ treated area can be removed, and not create an obstacle to the additional treatment, such as where a partial or total joint replacement is desired. Advantageously, the SCP™ treatment may be provided as a first or initial treatment, reserving for the future and possibly forestalling until a later date than otherwise might be the case more invasive treatments such as partial or total joint replacement.

A number of treatment modalities, and associated devices, instruments and related methods of use for performing SUBCHONDROPLASTY™ are disclosed in the aforementioned publications. These treatment modalities may be used alone or in combination.

In one treatment modality, the subchondral bone in the region of the bone marrow lesion or defect can be strengthened by introduction of a hardening material, such as a bone substitute, at the site. The bone substitute may be an injectable calcium phosphate ensconced in an optimized carrier material. In SCP™, the injected material may also serve as a bone stimulator that reinvigorates the desired acute bone healing activity.

For example, polymethylmethacrylate (PMMA) or calcium phosphate (CaP) cement injections can be made at the defect site. PMMA injection may increase the mechanical strength of the bone, allowing it to withstand greater mechanical stresses. CaP cement injection may also increase the mechanical strength of the bone, while also stimulating the localized region for bone fracture repair. In one embodiment, the injection can be made parallel to the joint surface. In another embodiment, the injection can be made at an angle to the joint surface. In yet another embodiment, the injection can be made below a bone marrow lesion. Preferably, the injection is made without disrupting the joint surface.

In another treatment modality, the subchondral bone region can be stimulated to trigger or improve the body's natural healing process. For example, in one embodiment of this treatment modality, one or more small holes may be drilled at the region of the defect to increase stimulation (e.g., blood flow, cellular turnover, etc.) and initiate a healing response leading to bone repair. In another embodiment, after holes are drilled an osteogenic, osteoinductive, or osteoconductive agent may be introduced to the site. Bone graft material, for example, may be used to fill the hole. This treatment modality may create a better load-supporting environment leading to long term healing. Electrical or heat stimulation may also be employed to stimulate the healing process of a chronically injured bone. Chemical, biochemical and/or biological stimulation may also be employed in SCP™. For instance, stimulation of bone tissue in SCP™ may be enhanced via the use of cytokines and other cell signaling agents to trigger osteogenesis, chondrogenesis, and/or angiogenesis to perhaps reverse progression of osteoarthritis.

In yet another treatment modality, an implantable device may be implanted into the subchondral bone to provide mechanical support to the damaged or affected bone region, such as where an insufficiency fracture or stress fracture has occurred. The implant may help create a better load distribution in the subchondral region. In the knees, the implant may support tibio-femoral compressive loads. In addition, the implant may mechanically integrate sclerotic bone with the surrounding healthy bone tissue. The implants may be place in cancellous bone, through sclerotic bone, or under sclerotic bone at the affected bone region. The implant may also be configured as a bi-cortical bone implant. In one embodiment, one side of the implant can be anchored to the peripheral cortex to create a cantilever beam support (i.e., a portion of the implant is inserted into bone but the second end stays outside or near the outer surface of the bone). The implant may be inserted using a guide wire. In one example, the implant may be inserted over a guide wire. In another example, the implant may be delivered through a guide instrument.

The implant may further be augmented with a PMMA or CaP cement injection, other biologic agent, or an osteoconductive, osteoinductive and/or osteogenic agent. The augmentation material may be introduced through the implant, around the implant, and/or apart from the implant but at the affected bone region, such as into the lower region of a bone marrow lesion or below the lesion. For example, the implant may act as a portal to inject the augmentation material into the subchondral bone region.

While each of the above-mentioned treatment modalities may be administered independent of one another, it is contemplated that any combination of these modalities may be applied together and in any order so desired, depending on the severity or stage of development of the bone defect(s). Suitable implantable fixation devices for the surgical treatment of these altered bone regions or bone defects, especially at the subchondral level, are disclosed in co-pending and co-owned U.S. Patent Application Publication No. 2011/0125265 entitled "IMPLANTABLE DEVICES FOR SUBCHONDRAL TREATMENT OF JOINT PAIN," U.S. Patent Application Publication No. 2011/0125264 entitled "IMPLANTABLE DEVICES FOR SUBCHONDRAL TREATMENT OF JOINT PAIN," and U.S. Patent Application Publication No. 2011/0125272 entitled "BONE-DERIVED IMPLANTABLE DEVICES FOR SUBCHONDRAL TREATMENT OF JOINT PAIN," all of which were filed on Nov. 19, 2010, the contents of which are herein incorporated in their entirety by reference. These devices and instruments can be use in combination with cements or hardening materials commonly used to repair damaged bone by their introduction into or near the site of damage, either to create a binding agent, cellular scaffold or mechanical scaffold for immobilization, regeneration or remodeling of the bone tissue. As previously stated, treatment of the bone defect at the subchondral level preferably is performed without disrupting the joint surface.

In general, the present disclosure provides embodiments related to instruments and associated methods for the surgical treatment of a joint, and particularly to a bone defect at that joint region. More specifically, the embodiments relate to instruments for navigating and positioning devices into an area sufficiently near a defect of the joint. Even more specifically, the instruments and associated methods for use are suitable for the repair of a femoral bone of a knee joint. These instruments and devices may be used in a manner consistent with the subchondral procedures previously described.

In a healthy joint such as a tibio-femoral joint, the compressive load between the contact bones (i.e., the femur and the tibia) is properly distributed, thus keeping the contact stresses in the cartilage to a reasonably low level. As the cartilage starts to wear out or degenerate locally, the tibio-femoral contact area reduces and starts to get localized at the site of the cartilage defect. The localization of the stresses may also occur due to varus or valgus deformity. Sometimes, the condition may occur because of osteoporosis, where bone becomes weak and is no longer able to support normal loads. This condition leads to higher localized contact stresses in the cartilage, and the subchondral region below the cartilage. Once the stresses reach beyond a certain threshold level, it leads to defects like bone marrow lesions and edema, and perhaps generates knee pain. If the problem persists, the high contact stresses can lead to sclerotic bone formation as well. The presence of sclerotic bone can compromise vascularization of the local area, and also create a mechanical mismatch in the bone tissue. This mismatch may start to expedite degeneration of all parts of the joint leading to increased levels of osteoarthritis.

Pain associated with osteoarthritic joints can be correlated to bone defects or changes at the subchondral level. In particular, bone defects such as bone marrow lesions, edema, fissures, fractures, etc. near the joint surface lead to abnormal stress distribution in the periarticular bone, which may or may not cause inflammation and generate pain. By altering the makeup of the periarticular bone (which may or may not be sclerotic) in relation to the surrounding region, it is possible to change the structural integrity of the affected bone, leading to a resolution of the inflammation. Treatment of the bone in an effort to alter the structural makeup of the affected periarticular bone leads to reduced inflammation and pain has proven to be successful. Over time, restoration of normal physiologic stress distribution can be achieved in load bearing joints such as the hip and knee, and mechanical congruity restored, thereby resulting in healing of the inflammation and reduction or elimination of pain.

As previously mentioned, there is a need for surgical instruments that will facilitate the application of the methodologies described above at the target site, or the bone defect, to be treated. Applicants have discovered instruments that are particularly suitable for accessing certain areas of the bone within the range of about 2-15 mm from the bone surface, and more commonly about 5-10 mm from the bone surface, such as the articular surface or the subchondral bone area, and therefore require more precise defect location features. These instruments are also particularly suited to deliver bone substitute material, devices, implants, etc. without disrupting the joint surface. Accordingly, the present disclosure provides suitable instruments and associated methods for the surgical treatment of these bone defects, especially at the subchondral level near sclerotic bone.

In general, the embodiments relate to instruments and associated methods for the surgical treatment of a joint, and particularly to a subchondral bone defect at that joint region. More specifically, the embodiments relate to instruments that allow fast, easy, precise, and controllable delivery or removal of materials subchondrally to a bone joint being treated.

Turning now to the drawings, FIG. 1 shows an exemplary embodiment of a delivery instrument of the present disclosure. The delivery instrument may take the form of an injection needle 100 that is configured to deliver a material to a subchondral area of a bone joint to be treated. The injection needle 100 may include a trocar tip 102, an elongate shaft 106 and an attachment end 104. The attachment end 104 may be threaded for threaded connection to other delivery instruments or tools, such as a syringe. The trocar tip 102 may be closed (as shown), though the elongate shaft 106 may be cannulated. The tip 102 may be a drill point or cutting blade, if so desired, instead of the trocar tip. As further shown, the region near the tip 102 may also include one or more holes 108 for delivery of a material out of the needle 100 (i.e., the needle 100 is fenestrated). The elongate shaft 106 may also include surface features that would allow the user to thread the injection needle 102 into bone tissue during use. These surface features may comprise helically cut grooves 110 on the outer surface of the elongate shaft 106 and are recessed below the outer surface. Alternatively, the surface features may comprise threads on the outer surface of the elongate shaft 106 and are raised above the outer surface.

In use, the injection needle 100 may be threaded into the bone to be treated. The tip 102 may be configured to pierce hardened, sclerotic bone. The threading of the injection needle 102 allows the user some level of control and stability during the injection of a material to the subchondral area to be treated. For example, the threads 110 may serve as a seal, preventing the backflow of material out of the insertion portal. In addition, the threads 110 may also provide control, preventing the user from going too deep into the bone tissue. It is contemplated that the threads 110 would be employed in the cortical bone region of the bone to be treated.

Figure 2A:
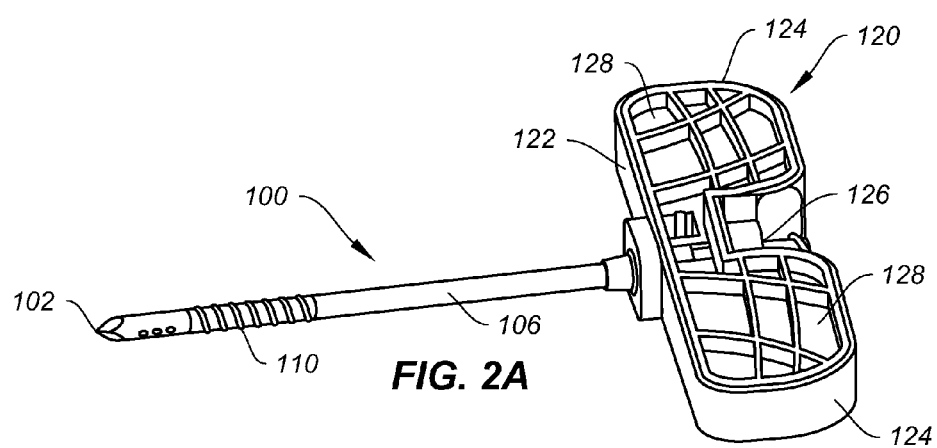
FIG. 2A shows the injection needle of FIG. 1 in use with a stabilization instrument.

FIG. 2A illustrates the injection needle 100 of FIG. 1 in use with a stabilization instrument that, in the present example, may take the form of a handle 120. The handle 120 may comprise a main body 122 having gripping portions 124 and a central channel 106 for receiving the injection needle 100. The gripping portions 124 may include a gripping surface 128 to facilitate manually controlling the threading of the injection needle 100 into bone tissue.

Figure 2B:
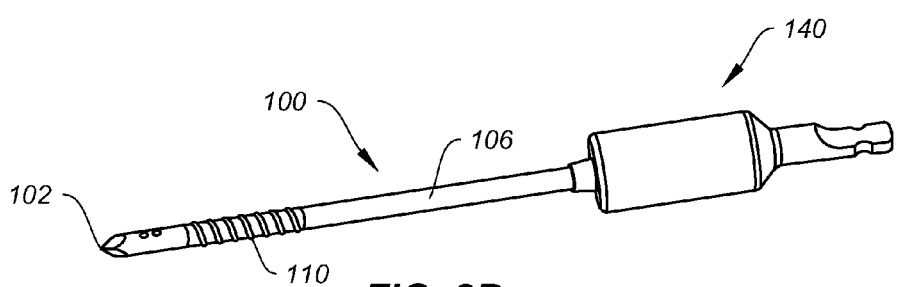
FIG. 2B shows the injection needle of FIG. 1 in use with an instrument connection.

FIG. 2B illustrates the injection needle 100 of FIG. 1 in use with an additional component, an instrument connection 140. This instrument connection 140 may be configured to slide over and secure onto the threaded end 104 of the injection needle 100, or it may be configured to attach to the injection needle 100 at the base of the connection 140. In the present example, the instrument connection 140 may be a drill adapter that is configured to allow attachment of the injection needle 100 to a drill or power driver.

Figure 3A:
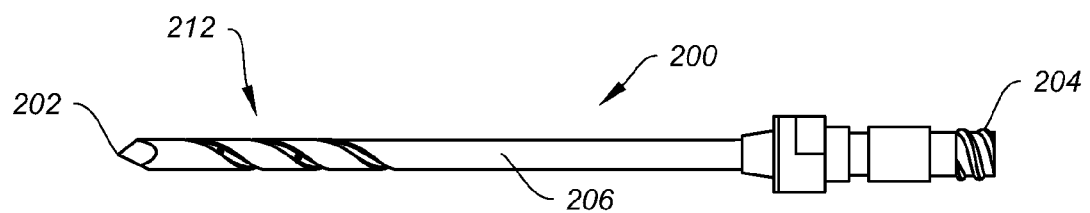
FIG. 3A shows a perspective view of another injection needle of the present disclosure.

FIG. 3A shows another exemplary embodiment of an injection needle 200 of the present disclosure. The injection needle 200 shares similar features with injection needle 100, and has a sharp tip 202, an elongate shaft or body 206 and a tool attachment end 204. The closed end, sharp tip 202 may be a trocar tip, drill point or cutting blade, as desired. The elongate body 206 may be cannulated, and the attachment end 204 may be threaded to allow threaded connection to other instruments. Like injection needle 100, the present injection needle 200 may also be fenestrated, with a helix port region 212 comprising a helical groove or spiral cutout 214 inside of which can reside injection ports or holes 216, as shown in greater detail in FIG. 3B. The helical cutout 214 may serve as threads or other surface enhancement, enabling the injection needle to be threaded into bone tissue while the holes 216 may allow the delivery of a material to the subchondral area of the bone to be treated. It is contemplated that the helical cutout 214 may also serve an additional function of directing or guiding the flow of material out of the holes 216.

Figure 3B:
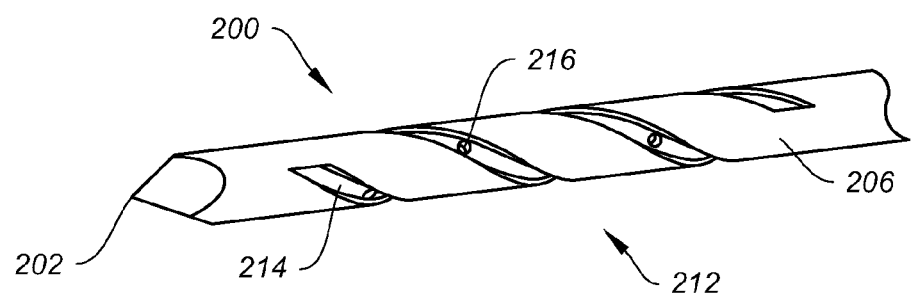
FIG. 3B shows an enlarged view of the tip of the injection needle of FIG. 3A.
Figure 4A:
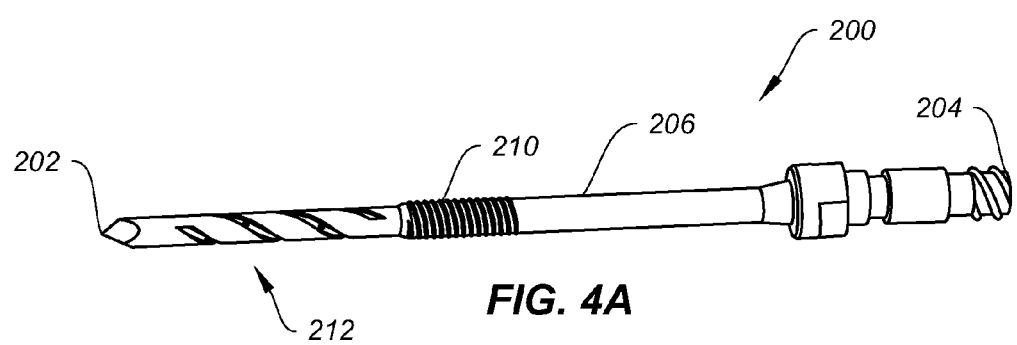
FIG. 4A shows a perspective view of yet another injection needle of the present disclosure.
Figure 4B:
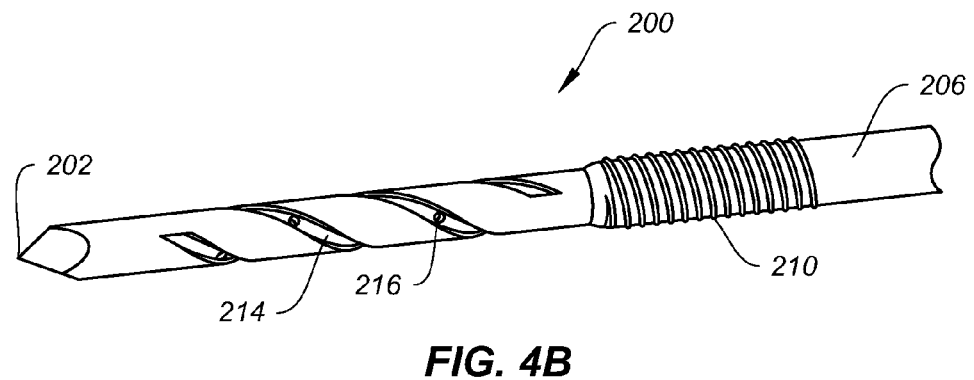
FIG. 4B shows an enlarged view of the tip of the injection needle of FIG. 4A.

FIGS. 4A and 4B show still another exemplary embodiment of a delivery instrument in which the injection needle 200 of FIGS. 3A and 3B includes threads 210. In this embodiment, the injection needle 200 may be threaded into the bone tissue during use. For example, the injection needle 200 may be threaded into the outer cortical bone for additional control or stability, as previously discussed.

Figure 5A:
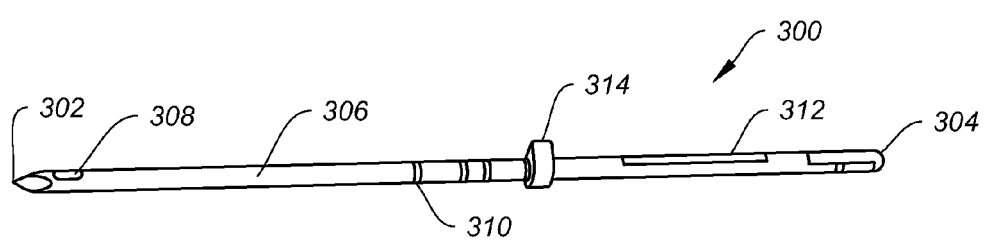
FIG. 5A shows a fenestrated pin.

FIG. 5A shows yet another exemplary embodiment of a delivery instrument of the present disclosure that may take the form of a semi-cannulated pin 300 that can be drilled into bone and deliver material in a controlled manner. The pin 300 may include a sharp cutting tip 302 that can be a trocar tip, drill tip or cutting blade. The tip 302 extends into an elongate body 306 and terminates into an instrument attachment end 304. As with the previous delivery instruments, the pin 300 may be fenestrated and include a hole 308 near the tip 302. Along the shaft 306 may be etchings or indicia 310 that indicate depth or the distance from the tip, or relative distance to another marker. The etchings 310 could also correspond to the holes 308 or fenestrations. Another visual marker or window 312 may also be provided on the shaft 306, as well as a tactile marker 314 that may correspond with the fenestration(s) and indicate directionality to the user. This tactile marker 314 could be a unidirectional protrusion that corresponds to the orientation of the hole 308 to help the user align the hole 308 during use.

It is contemplated that the pin 300 would include a tip 302 sharp enough to cut through bone tissue. The fenestration(s) or holes 308 would feed to the back of the pin 300, with the etchings 310 facilitating the control of delivery. Further, the attachment end 304 would allow connection to another instrument such as a drill or syringe. For example, the attachment end 304 could cooperate with a Luer lock adapter or other similar adapters.

Figure 5B:
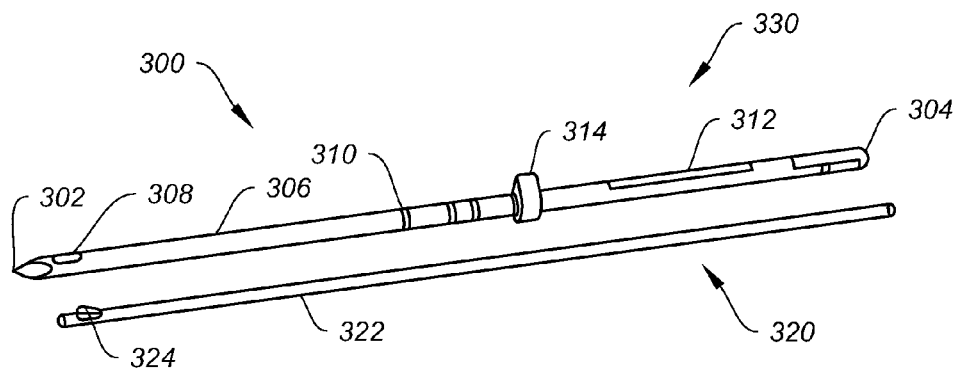
FIG. 5B shows a delivery system comprising the fenestrated pin of FIG. 5A with an associated internal pin.

FIG. 5B shows a system 330 comprising the pin 300 of FIG. 5A along with a secondary pin 320 having an elongate shaft 322 and a spring-type tong 324 or other blocking mechanism that may block the hole or fenestration 308 of pin 300 when the secondary pin 320 is inside. This secondary pin 320 may be placed inside the first pin 300 and rotated about so as to control the opening and closing of the hole or fenestration 308, and thereby the delivery of material out of the system 330. Additionally, the secondary pin 320 also serves other functions. In one example, the secondary pin 320 may be inserted into primary pin 300 and the tong 324 adjusted so as to block the fenestration 308 prior to insertion. Blockage of the fenestration 308 prevents the hole from getting clogged as it is being drilled inside the body, as material may become trapped in the hole if it is not covered. In another example, the secondary pin 320 may additionally be used to remove any remaining material inside the primary pin 300 after extrusion of material out of the hole or fenestration 308, acting as a plunger to rid the primary pin 300 of remaining material.

During use, the primary pin 300 may be drilled into bone with the internal or secondary pin 320 in place and configured as to cover the hole 308. The external etchings 310, window 312 and tactile marker 314 would be used to control depth and orientation of the pin 300. After the drill is taken off the pin 300, which may or may not have an AO connection, the secondary pin 320 would be removed by pulling out to leave a cannulation to the fenestrated hole 308. In this case, the tip 302 of the pin is solid and sharp, not cannulated. The cannulation is contemplated as reaching the hole or fenestration 308. Once the primary pin 300 has reached its final destination, the secondary pin 320 is removed and the primary pin 300 would be oriented by twisting it axially to direct the injectable material to be delivered. The hole 308 may be oriented by using the tactile and visual markings provided on the pin 300. A syringe could be connected to the attachment end 304 of the pin to inject the material to the desired bone area. After injection, the pin 300 may be removed from the bone.

Figure 6A:
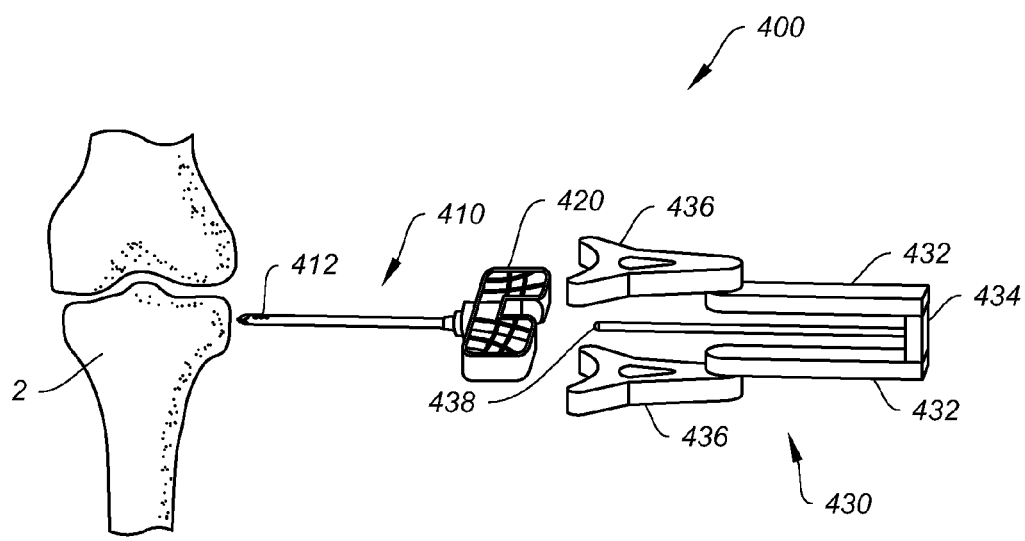
FIGS. 6A and 6B show a system comprising a stabilization instrument in use with a cannula of the present disclosure.
Figure 6B:
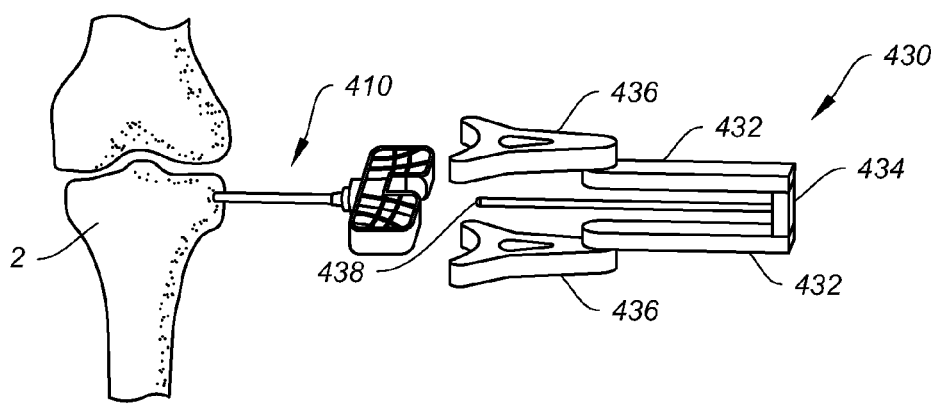

FIGS. 6A-6D show another exemplary delivery system that allows for injection with retraction. As shown in FIGS. 6A and 6B, the system 400 comprises a fenestrated cannula 410 having one or more fenestrations or holes 412 for delivering a material to a target bone site. The cannula 410 may be attached to a handle 420 as shown. The system may further include a stabilizer 430 that is configured to cooperate with the cannula 410. The stabilizer 430 may include a pair of bumpers 436 extending from a pair of arms 432 of the main body 434. Between the arms 432 and extending from the main body 434 may be a pin 438 that is configured to slide into the cannula 410, thereby stabilizing the cannula 410 as it is being inserted into the subchondral region of the bone 2 to be treated.

The pin 438 may be configured to have a tight fit with the cannula 410 in order to minimize backflow. The stabilizer 430 can be configured to rest against the patient's body, bone, muscle, fat, etc. with the tip of the pin 410 relatively close to the stabilizing surface, or the edge of the bumpers 436. For example, the bumpers 436 may comprise shaped portions that complement the surface of the patient's anatomy and allow the bumpers 436 to rest against the surface of bone. Additionally, the bumpers 436 may be movable or pivotable relative to the main body 434 to allow adjustment to the patient's anatomy. The stabilizer 430 is configured to allow the cannula 410 to be fully retracted to a state where the pin 438 is proud.

Figure 6C:
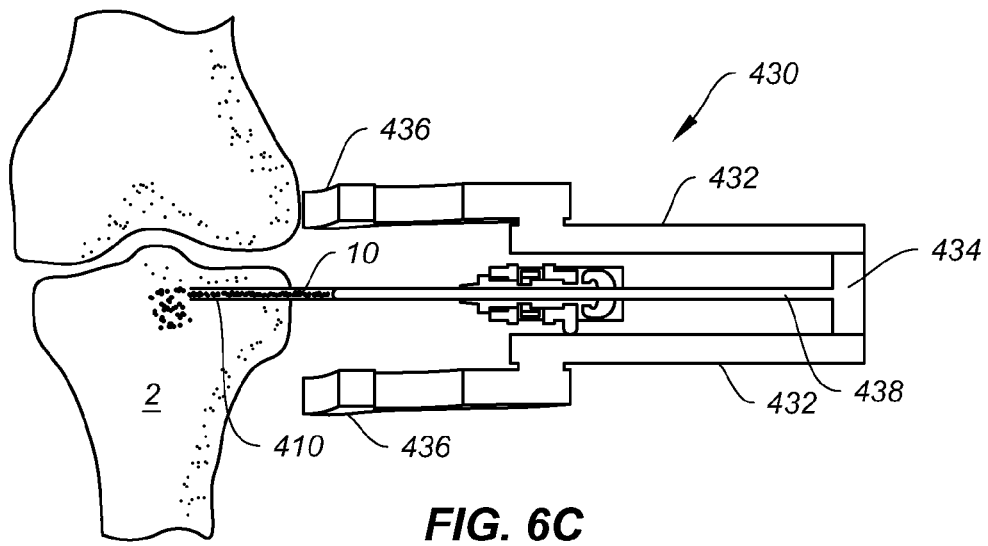
FIG. 6C is a cross-sectional view of the system of FIG. 6A during use.
Figure 6D:
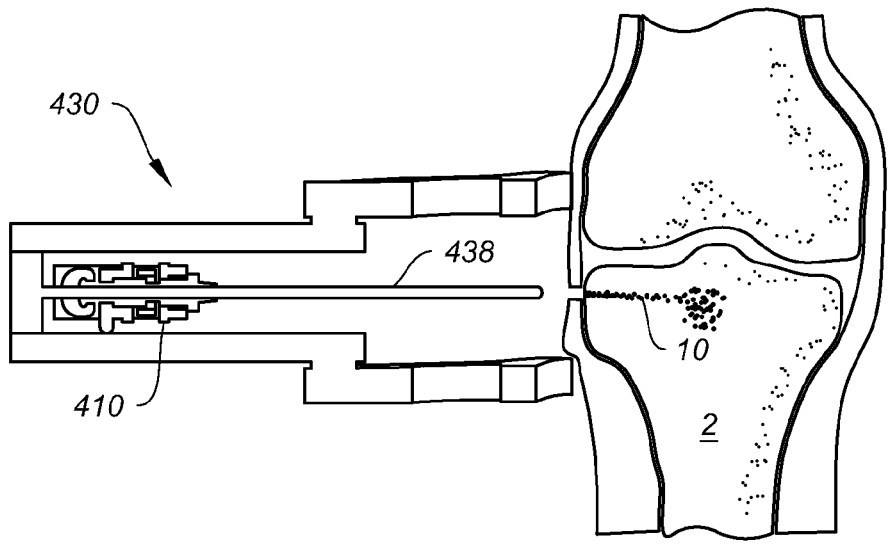
FIG. 6D is a cross-sectional view of the system of FIG. 6A after use.

FIGS. 6C and 6D show in greater detail a method of using the system 400 of the present disclosure. After insertion of the cannula 410 into the bone 2, an injectable material 10 may be deployed through the cannula 410. As shown, the stabilizer 430 can then be used. The pin 438 may be driven down into the cannula 410 forcing the injectable material 10 into the bone 2 until the bumpers 436 rest against the patient's body. At this point, the cannula 410 may be pulled back with respect to the stabilizer 430, which remains in place with respect to the patient. As the cannula 410 is retracted, the pin 438 would force more of the injectable material 10 into the bone 2, with the injection rate being proportional to the retraction rate. It is contemplated that the injectable material 10 will continue to eject so long as the cannula 410 continues to be pulled back. When the tip of the pin 438 is outside of the bone 2, the cannula 410 should be entirely retracted while the injected material 10 is left inside in the cavity left behind by the cannula 410.

Figure 7A:
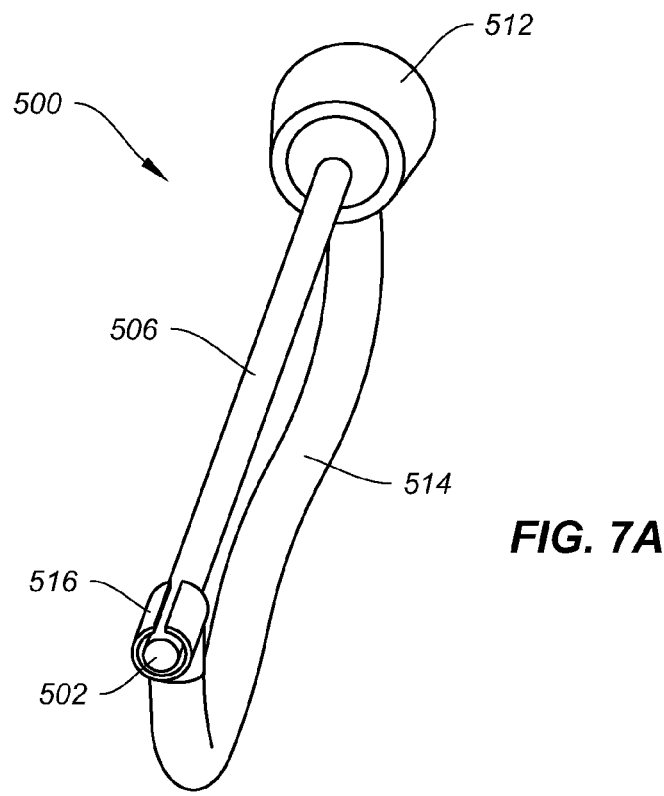
FIG. 7A shows a perspective view of another delivery instrument of the present disclosure having a fenestration cover.
Figure 7B:
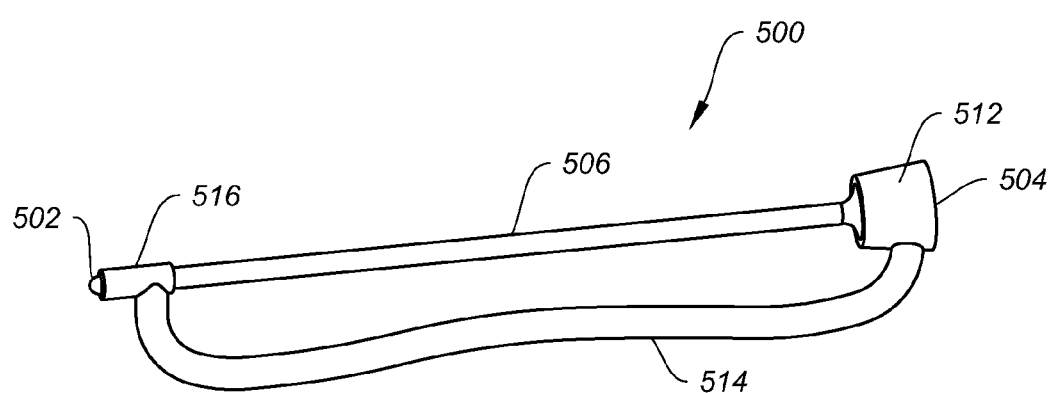
FIG. 7B shows another perspective view of the instrument of FIG. 7A with the fenestrations closed.
Figure 7C:
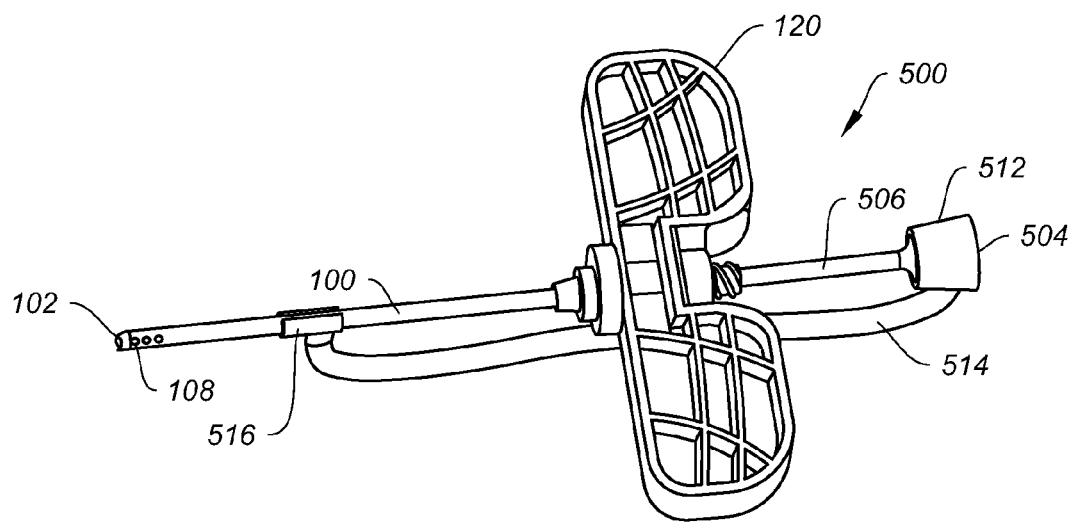
FIG. 7C shows a system comprising the instrument and fenestration cover of FIG. 7A with an injection needle and stabilization instrument.
Figure 7D:
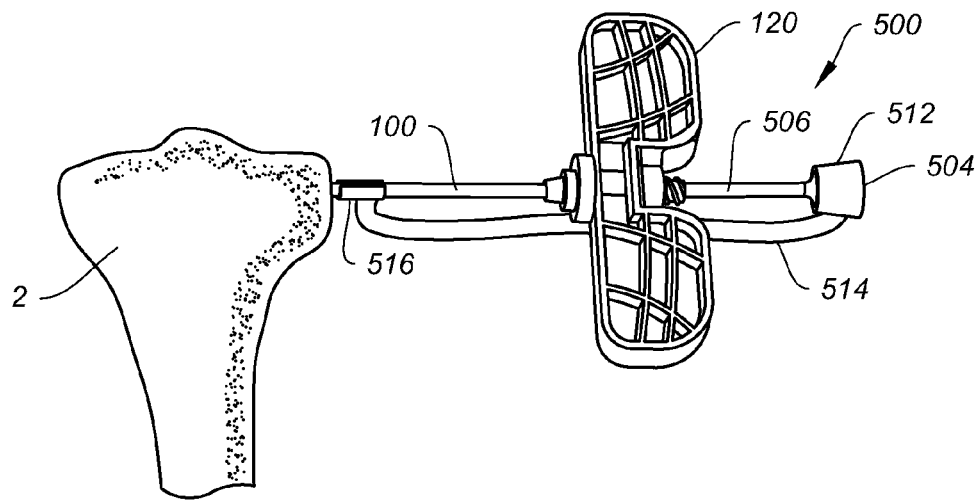
FIGS. 7D and 7E illustrate a method of using the system of FIG. 7C.
Figure 7E:
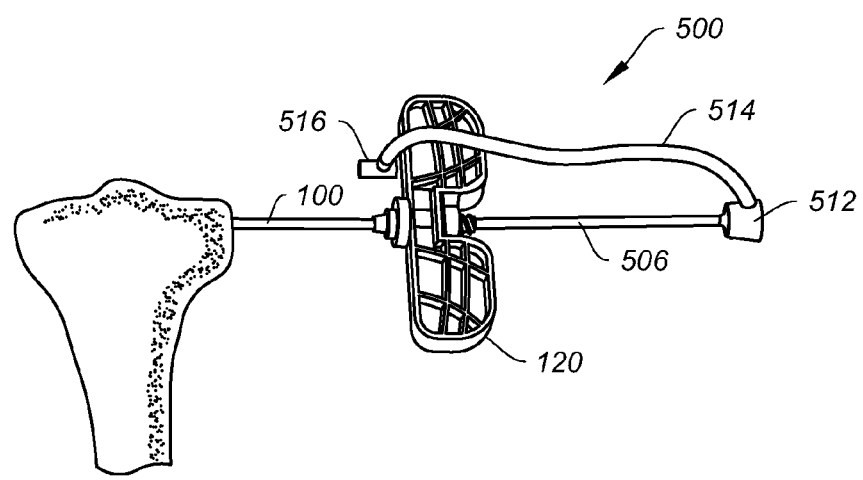

FIGS. 7A-7E illustrate still another exemplary embodiment of a delivery system of the present disclosure. FIGS. 7A and 7B illustrate an auxiliary delivery instrument 500 having a removable and slidable cover or sleeve 516 configured to cooperatively work with an injection needle, such as injection needle 100. The plunging device or delivery instrument 500 may be configured with a tip 502, elongate shaft 506 and device attachment end 504. The tip 502 may be configured for engagement with the injection needle, as shown in FIGS. 7C-7E, while the elongate shaft 506 may be cannulated. A syringe or injector system may be attached to the device attachment end 504 for delivery of material therethrough. The attachment end 504 may further include a band 512 from which extends a tether 514 that ends in the removable sleeve. In this exemplary embodiment, the removable sleeve may be a split ring 516, configured for sliding engagement with the tip 502 and shaft 506 of the instrument 500. The split ring 516 can snap over, and slide along, the shaft 506 to the tip 502, as well as along the shaft 106 of the injection needle 100 and over the fenestrations 108, in order to prevent the backflow of material out of the injection site. The tether 514 has a length sufficient to allow the split ring 516 to extend the length of the shafts of the instrument and injection needle when both are connected, as shown in FIGS. 7C-7E. The length of the split ring and tether could be such that the instrument 500 acts as a depth control stop or index, or provide needle depth control, when the needle is inserted into the bone 2.

FIGS. 7C-7E show the auxiliary delivery instrument 500 attached to a needle 100 and in use with the stabilizing instrument 120 of the present disclosure. This embodiment has a relatively smaller body contact area compared with previous embodiments. In a method of implementing the instrument 500, the needle 100 is first inserted into the bone 2 to be treated. An injectable material may then be injected through the needle 100, through instrument 500, and into the bone 2. As shown in FIG. 7C, the split ring 516 may slide over the elongate shaft of injection needle 100 and against the bone 2, covering the fenestrations 108. During use, the split ring 516 of the instrument 500 is pushed against the side of the bone 2, covering the fenestrations 108, to keep the injected material inside the bone 2 during the withdrawal of the needle 100. After the procedure has been completed, the split ring 516 may be snapped off the instrument 500 entirely, as shown in FIG. 7E.

In addition, the auxiliary delivery instrument 500 may also serve as a plunging device. In this example, the instrument 500 may be inserted within the injection needle and used to plunge the injection needle 100 as it is retracted from the bone 2. This allows the user to back fill the cavity or void in the bone 2 in a continuous, smooth motion. The split ring position can be indexed and fixed to the plunger device 500 such that the tip of the device 500 is held in a fixed position relative to the bone 2 when the split ring 516 is placed against the bone 2. For example, the plunger tip 502 can be positioned at the bone cortex such that the injectable material is evacuated from the needle tip up to the cortex, but not beyond the cortex. When the needle is removed, the injectable material remains in the cavity up to the boundary of the cortex. In other words, the split ring 516 can be referenced to the end of the plunger tip 502 that pushes the cement through to the end of the needle 100. When the split ring 516 is indexed against the bone 2 on the outside of the needle 100, the inner plunger or elongate shaft 506 is positioned at the bone at the same area.

Figure 8:
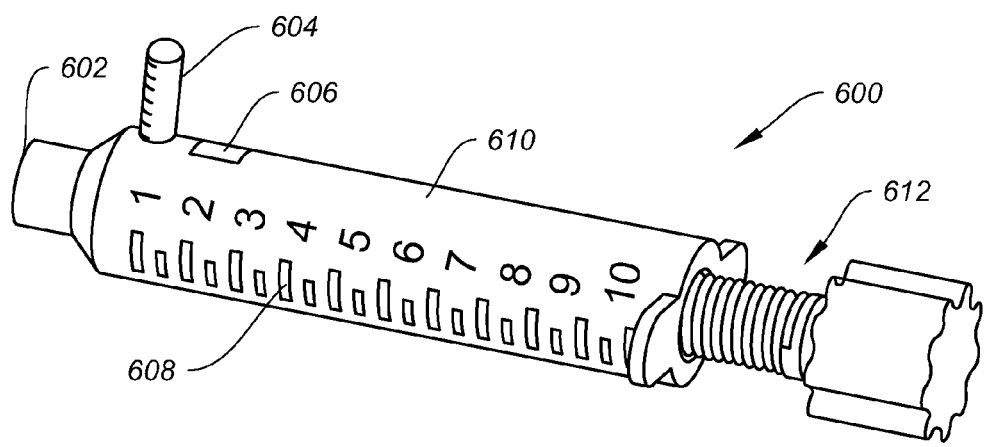
FIG. 8 shows a perspective view of a gauge and mechanical assist mechanism of the present disclosure.

As previously described, the methods of treatment of the present disclosure focus on the subchondral region of the bone joint. Accordingly, devices that can help determine the ideal range of pressure within a subchondral region are desired. This determination would eliminate variances in user subjectivity and render more predictable and repeatable results. FIG. 8 shows an embodiment of a gauge 600 that may be used with any one of the cannulas or pins of the present disclosure for this purpose. The gauge 600 would allow the user to accurately identify a desired range of pressure to achieve optimal patient results.

As shown, the gauge 600 of FIG. 8 may provide volumetric and pressure readings while also a mechanical assist. As shown, the gauge 600 may include an attachment end 602 that may be configured as a Luer lock connection, for instance. The attachment end 602 thus connects to any number of injectable material delivery instruments such as the cannulas and fenestrated pins disclosed. The gauge 600 also includes a mechanical pressure gauge 604, an electrical pressure gauge 606, and volumetric markers 608 that represent relative readings or represent remaining volume. The gauge 600 may comprise a transparent body or tube 610 that allows the user to visualize the contents of the gauge 600. In addition, a mechanical assist mechanism 612 may also be included. This mechanical assist mechanism 612 may be screw based, for example, as shown. Each half turn could be configured to represent a 1 cc volume, for example. Other mechanisms may of course be employed.

The gauge 600 allows the user even greater control over the amount of material injected into the bone 2 being treated, without losing the tactile pressure response normally experienced. This gauge 600 allows some pressure measurement outputs that could be similar to a pop-up timer or tire gauge, and could be either electrical or mechanical. For instance, the pressure readings could be mechanical and provide a go or no go signal via a blow out valve, and gauged to give a read out. Another example of an electrical mechanism is to have a constant read out from the gauge 600. Such a gauge 600 is intended to allow the user to control the volume and pressure of the material injected and still be able to exceed a digital pressure reading, if that was so desired.

Figure 9:
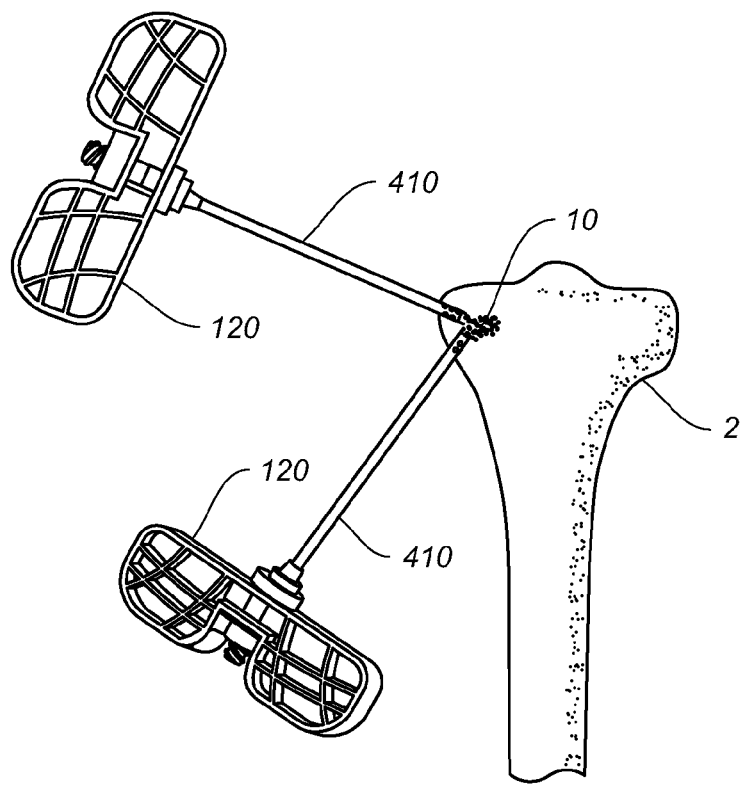
FIG. 9 shows a method of delivering and removing a material from an area of a bone joint to be treated.

FIG. 9 illustrates a method of using two or more cannulas 410 of the present disclosure to allow both injection and removal of material from a bone 2 to be treated. The cannulas 410 may be open ended or optionally they may include fenestrations. In the example shown, the cannulas 410 may be used with a stabilizing instrument 120 similar to those previously described. One cannula 410 may be inserted into the bone 2 and toward the subchondral space, to allow an injectable material 10 to be delivered. Another cannula 410 may be inserted so that the ends of the cannulas 410 are within the subchondral space. As material 10 is injected into the first cannula 410, the second cannula 410 may be utilized to remove any edema at the same site. The second cannula provides a port to the bone defect, such as an edema, such that during injection through the first cannula, fluid from the edema can escape through the second cannula. With this method, the risks or hazards of high pressure injection into the bone at the defect or edema can be averted.

Figure 10:
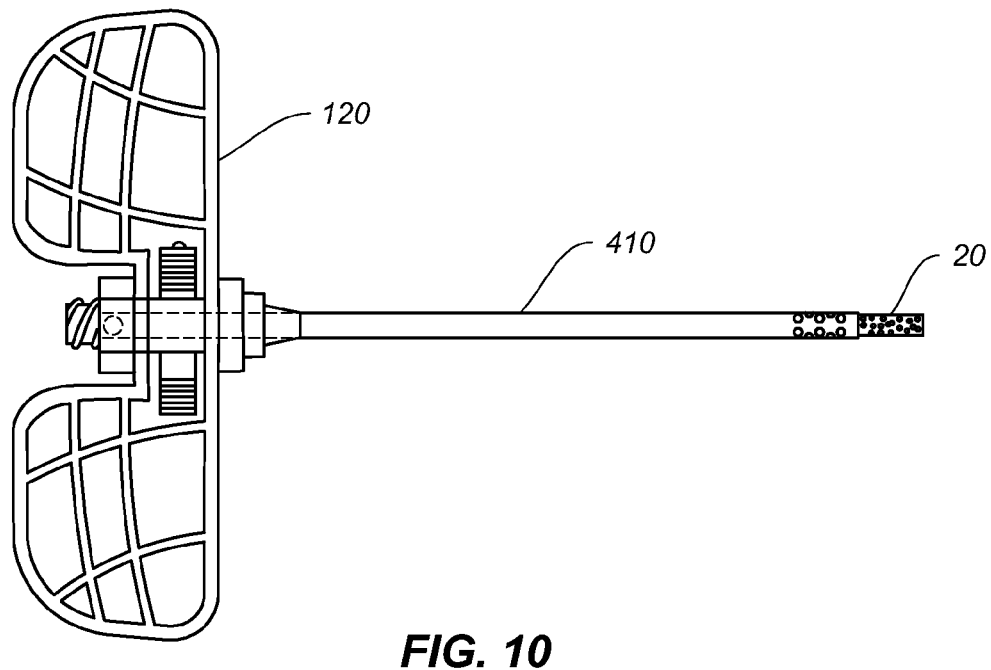
FIG. 10 shows a cannula with an attached bone plug.

FIG. 10 shows the same cannula 410 and stabilizing instrument 120 along with a fresh bone plug 20 created during the procedure. In one exemplary embodiment of using the fenestrated cannula 410 of the present invention, a pin may be inserted into bone, and the cannula 410 placed over the pin and driven into the bone to the end of the pin. The pin may be removed, while the cannula 410 pushed further into the bone tissue. The user could then tamp the fresh bone to the end to create a bone plug 20 at the end of the cannula 410. Once attached to the end of the cannula 410, the bone plug 410 would be able to block injected material from coming out of the tip end, instead of the intended fenestrations along the side or shaft of the cannula. The bone plug 410 could be used later to plug up the access portal created during drilling, if so desired. Additionally, visual markers can be provided on the pin to ascertain the insertion depth of the cannula placed over the pin, such that the cannula end is indexed to a position beyond the tip of the pin to capture bone material in the cannula. This bone material at the end of the cannula can then be impacted and used to create a bone plug at the end of the cannula.

Figure 11A:
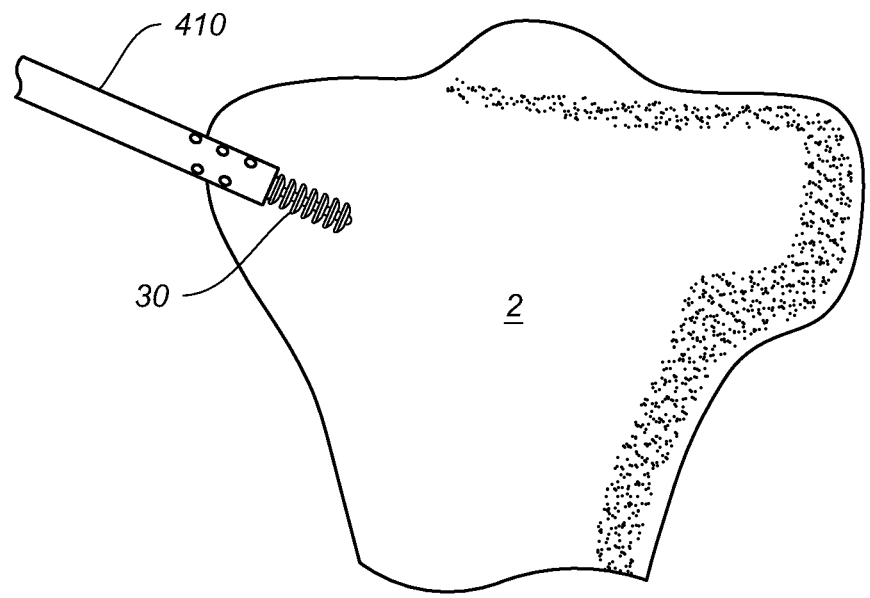
FIG. 11A shows a cannula with an artificial plug.
Figure 11B:
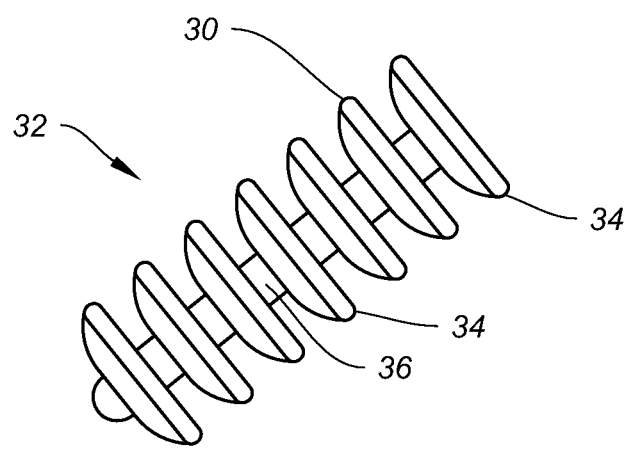
FIG. 11B shows an enlarged view of the artificial plug of FIG. 11A.

FIG. 11 shows still another method of treating a bone joint similar to the one previously described in FIG. 10, but now with a bone restricter or plug 30. For instance, the tip of the cannula 410 may include a bone restricter or plug 30 that acts to restrict the flow of materials. The plug 30 may comprise a main body 32 formed of a plurality of flanges 34 attached to a central stem 36, as shown in FIG. 11B. The plug 30 may be formed of resorbable or absorbable or degradable material. The plug may further be formed of a flexible material such as PLGA, for example. Initially the plug 30 may be retained in the cannula 410 whereupon it can be delivered into the subchondral space of the bone joint to be treated, and allowed to expand. This plug 30 may be delivered at the same time the injectable material is injected, or before the material is injected, as desired. During injection, the plug 30 would serve to prevent material from being ejected out the tip instead of the intended fenestrations on the side of the cannula 410. The plug 30 could also be inserted into the access portal created for the insertion of the cannula 410 after injection, in order to prevent any backout of material.

Figure 12:
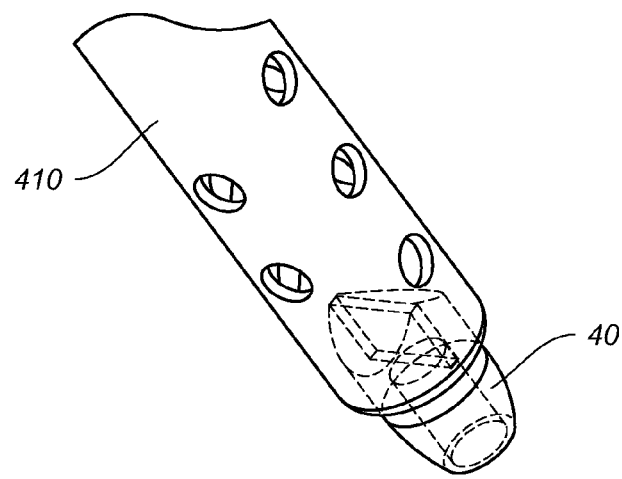
FIG. 12 shows a partial exposed view of a cannula with a valve.

FIG. 12 illustrates an embodiment of the fenestrated cannula 410 with a one-way valve 40 that can be attached at one end of the cannula 410 to allow the passage of a pin or wire, but would otherwise restrict the flow of any backflow of material or bone substance through the cannula 410. The valve 40 could be configured to attach to the tip end of the cannula 410, allow for the pin to slide over but closes once the pin has been removed. Use of the valve 40 would force bone substance to flow through the fenestrations of the cannula 410.

Figure 13:
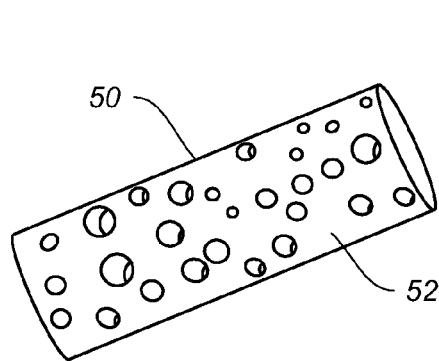
FIG. 13 shows a perspective view of a highly porous implant of the present disclosure.
Figure 14:
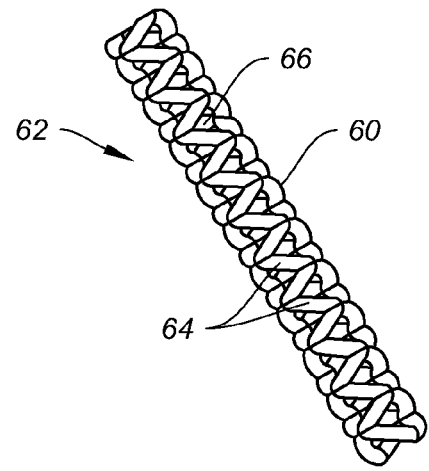
FIG. 14 shows a perspective view of a highly porous implant of the present disclosure.

FIGS. 13 and 14 represent highly porous implants 50, 60 that may be housed internally within the cannula or other delivery instrument. These implants 50, 60 would have a highly porous geometry and allow the flow of material out of the cannula but also redirect or induce dispersion of the material during injection. Similar to the plugs 20, 30 described above, these implants may also serve to prevent flow of material out through the tip of the cannula, instead of the sides through fenestrations. The implants 50, 60 may be formed of a resorbable, absorbable or degradable material, such as calcium phosphate or collagen, for example. As shown in FIG. 13, the highly porous implant 50 may have a body 52 formed as a generally cylindrical plug. In FIG. 14, the highly porous implant 60 may comprise a more structured body 62. The structured body 62 may have a mesh-like or lattice-like pattern, with interconnected struts 64 and voids or interstices 66, in between.

Figure 15A:
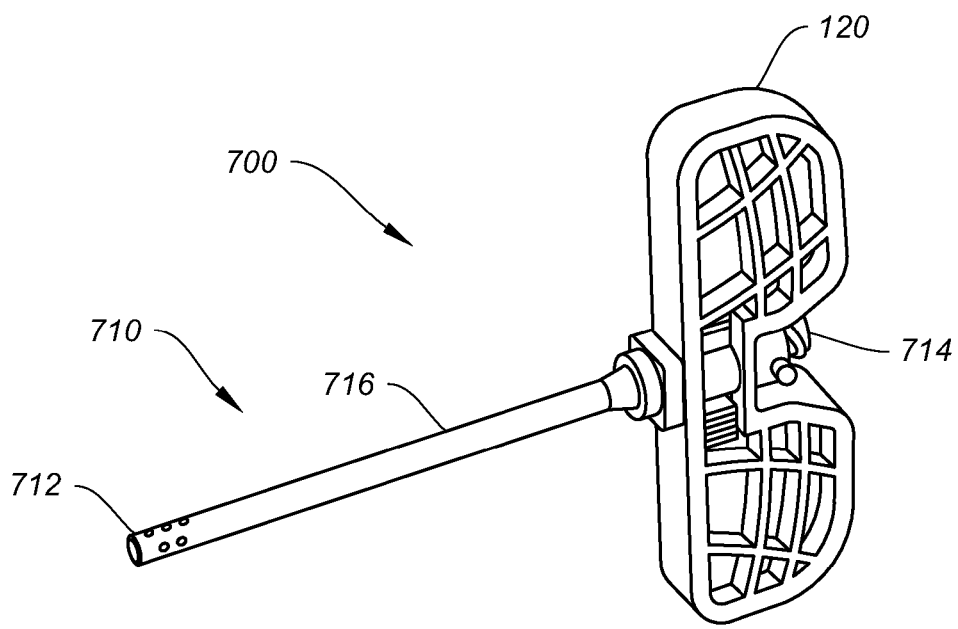
FIG. 15A shows a first component of still yet another exemplary embodiment of an injection material delivery system of the present disclosure.
Figure 15B:
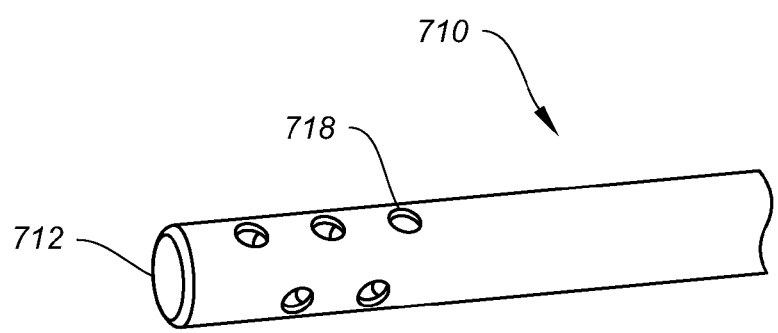
FIG. 15B shows an enlarged view of the first component of FIG. 15A.

FIG. 15A shows the first component of an injectable material delivery system 700 comprising an outer cannula 710 with an attachment end 714, shaft 716, and open-ended tip 712 that allows the outer cannula 710 to be used over a guidewire. Fenestrations or holes 718 are provided on the shaft 716 for the delivery of an injectable material, as shown in detail in FIG. 15B. As shown in FIG. 15A, the cannula 712 may be used with a handle 120 similar to the one previously described.

Figure 16A:
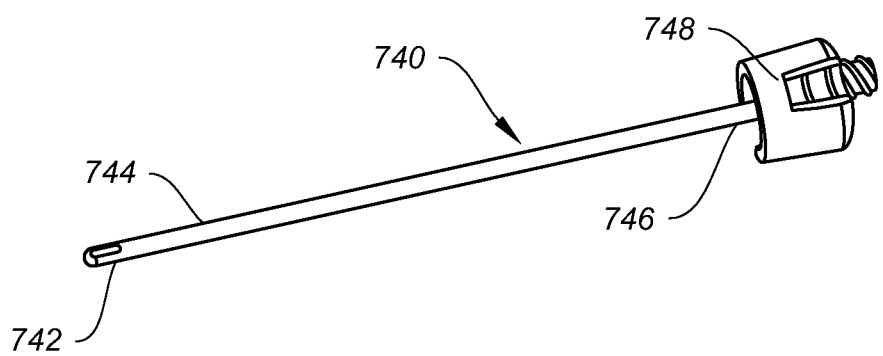
FIG. 16A illustrates another component of the injection material delivery system of FIG. 15A.
Figure 16B:
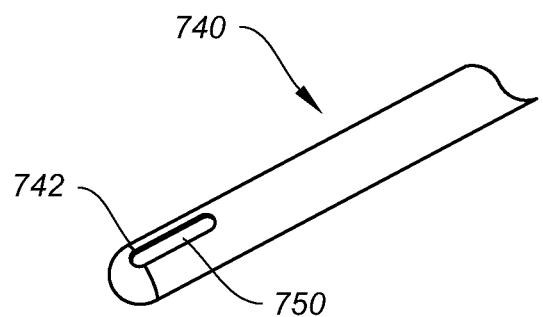
FIG. 16B shows an enlarged view of the second component of FIG. 16A.

FIG. 16A shows the second component of the injectable material delivery system 700 comprising an inner rod 740 having a first, closed tip 742, a shaft 744, and an attachment end 746. An end cap 748 can be provided on the attachment end that is configured to attach to a Luer lock, for example, for connection to a syringe. Near the closed tip 742 the rod 740 may have a slot or opening 750 that corresponds to the fenestrations, such that the slot or opening 750 aligns with the holes 718 of the outer cannula 710 when the inner rod 740 is inserted inside.

Figure 17A:
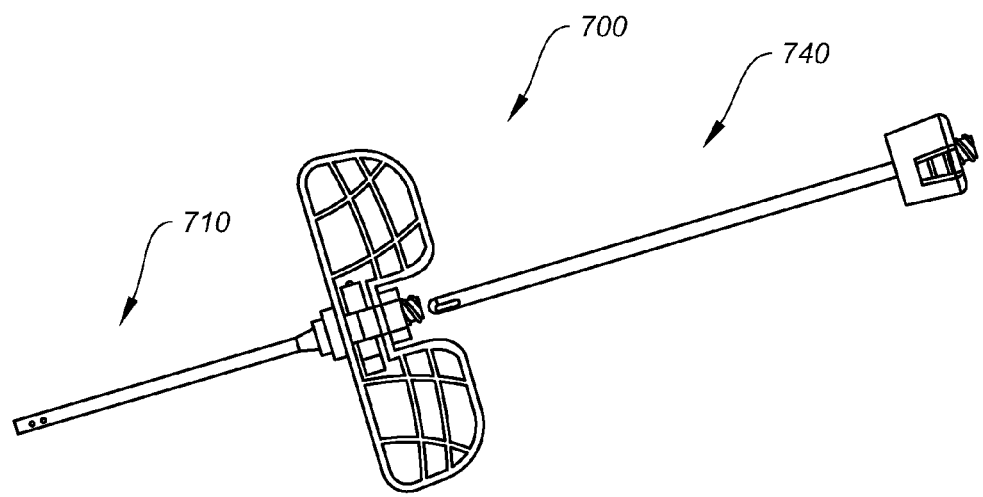
FIG. 17A shows an exploded view of the system of FIG. 15A.
Figure 17B:
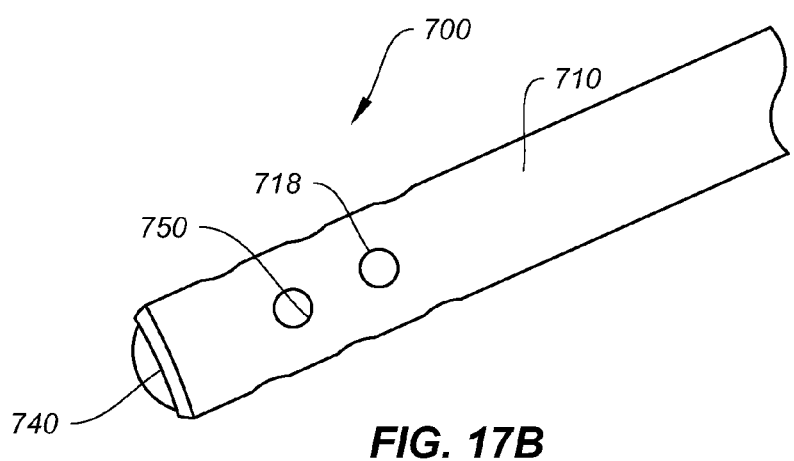
FIG. 17B shows an enlarged view of the system of FIG. 15A together.

As can be seen in FIGS. 17A and 17B, in which both the first and second components 710, 740 of the injectable material delivery system 700 are shown, the inner rod 740 is configured to slide into the outer cannula 710. When the inner rod 740 is inserted to the end of the tip 712 of the cannula 710, the slot or opening 750 of the inner rod 740 can be rotated so that the opening 750 aligns with the fenestrations 718, thereby opening up the holes 718 and allowing material to escape, or not align with the fenestrations 718, thereby closing off the holes 718 and preventing material from escaping.

In one exemplary method of use, the outer cannula 710 may be inserted into bone with the use of a guide wire, after which the guide wire is removed. The second component, the inner rod 740 is then inserted into the outer cannula 710. The inner rod 740 may form a very tight seal with the outer cannula 710, mating perfectly with it to prevent inadvertent injection material extrusion between the spaces. In one embodiment, the inner rod 740 may have a trocar tip so that the combined outer cannula 710 and inner rod 740 can be inserted together over a guide wire. The inner rod 740 can then be adjusted to align the opening 750 of the inner rod 740 with the fenestrations 718 of the outer cannula 710 (in the "open" position.)

Figure 18:
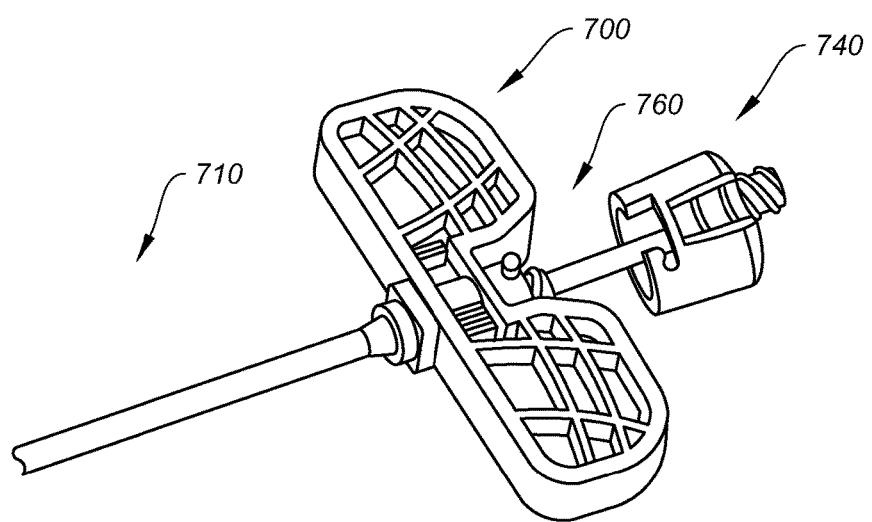
FIG. 18 shows a locking mechanism of the system of FIG. 15A.

Once the inner rod 740 is in position, the two components can be locked together. FIG. 18 shows an exemplary locking mechanism 760 comprising a cutout or hook on the end cap 748, and knob or peg on a handle component similar to those previously described and attachable to the outer cannula 710, on the respective components such that one component can be twisted relative to the other to enable the hook to latch onto the knob. For example, the inner rod 740 may be rotationally keyed or locked to the outer cannula 710 to ensure that the openings are aligned. Alternatively, the inner rod end cap 748 may be rotated or indexed to a specific position relative to the outer cannula 710 such that the opening 750 of the inner rod 740 is aligned to only some of the fenestrations 718 in one section or quadrant of the outer cannula 710, thereby allowing directional control of the ejection of material.

After the two components are secured together, the end cap 748 may be attached to an injection device such as a syringe, for example. Injectable material may then be injected through the inner rod 740. The material will follow the path of least resistance, and therefore exit at the end of the system 700 through the orifice created by the aligned hole 750 and the fenestrations 718.

Figure 19A:
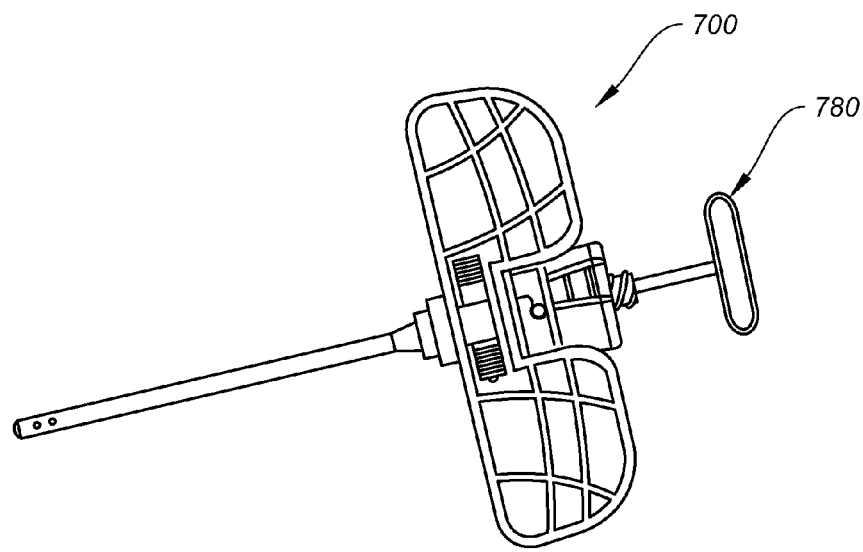
FIG. 19A shows the system of FIG. 15A in use with a plunger.
Figure 19B:
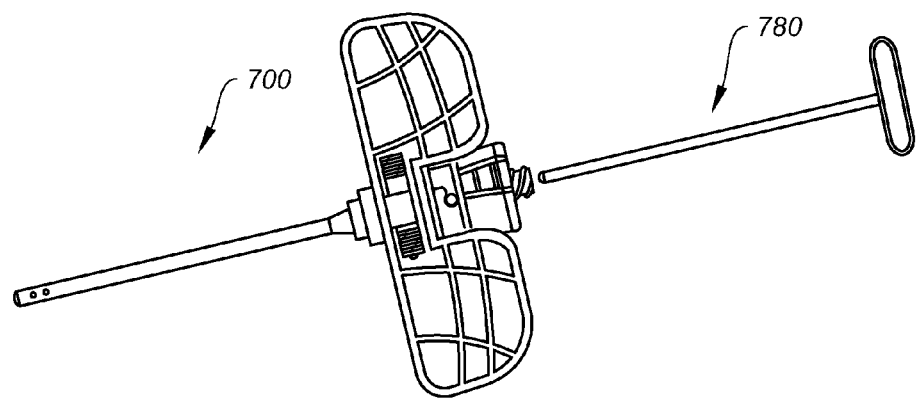
FIG. 19B shows an exploded view of FIG. 19B.

To clear the inner rod 740 of all of the injectable material, a plunger 780 may be inserted through the inner rod 740, as shown in FIG. 19A. The plunger 780 may comprise an elongate rod extending from a handle, and should make a close fit with the inner rod 740 to effectively clear all residual material inside the rod 740. The plunger 780 and inner rod 740 may then be removed, leaving the outer cannula 710 behind. Next, a plug such as an allograft plug, for example, may be inserted into the outer cannula 710 and pushed into the bone using the plunger 780, like in FIG. 19B.

It is contemplated that the back pressure on the injected material would diffuse around the plug and fill up any voids.

In an alternative method, after the injection of material and the removal of the plunger 780 and inner rod 740, a cannulated plug may be inserted down through the cannula, and a cannulated plunger or other pushing device used to push down the cannulated plug, which may be an allograft plug, for example. In some embodiments, the guide wire may be one having a very small diameter to allow for a cannulated plug with a small opening.

In still another method, after the injection of material and the removal of the plunger 780 and inner rod 740, a guide wire can be reinserted through the remaining outer cannula 710. The outer cannula 710 can then be removed, leaving just the guide wire in place. A plug can then be slid down the guide wire and pushed into place to cover the opening or void.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

What is claimed is:

1. An injection needle configured to deliver material to a subchondral area of a bone joint to be treated, comprising:
a closed first end comprising a sharp, pointed tip sufficient to pierce bone tissue, a second end comprising a tool attachment end, and an elongate shaft extending therebetween and including a cylindrical outer surface defining an outer diameter, the shaft being partially cannulated and having one or more helical grooves near the first end that are recessed below the outer surface of the elongate shaft and that define a root diameter that is less than the outer diameter, the needle further comprising one or more external threads located at the tool attachment end, one or more holes for ejection of an injectable material therethrough, and a drill adapter, formed as a separate component and structured for detachable engagement with the one or more external threads at the tool attachment end.

2. The injection needle of claim 1, wherein the one or more holes reside between the one or more helical grooves and the tip.

3. The injection needle of claim 1, wherein the drill adapter includes a base portion configured for attachment to the tool attachment end and a shank portion configured to engage with a rotary drilling device.

4. The injection needle of claim 1, wherein the tip is a trocar tip.

5. The injection needle of claim 1, wherein the tip is a drill tip.

6. The injection needle of claim 1, wherein the tip is a cutting blade.

7. The injection needle of claim 1, further comprising a handle.

8. The injection needle of claim 7, wherein the handle includes at least one gripping portion to facilitate insertion of the injection needle into bone.

9. The injection needle of claim 1, wherein the drill adapter further comprises an elongate shank configured to extend away from the tool attachment end and including a bit portion sized and shaped for engagement with a drill or power driver.

10. The injection needle of claim 1, wherein the one or more helical grooves define a grooved shaft section disposed between the first end and the second end, and wherein the one or more holes are disposed between and longitudinally spaced from the grooved shaft section and the tip.

11. The injection needle of claim 10, further comprising a handle, wherein the handle includes a main body, a pair of gripping portions extending from opposing sides of the main body, and a central channel adapted to receive the tool attachment end of the injection needle therein such that, when the handle is coupled to the injection needle, a portion of the tool attachment end extends out of the central channel to expose the one or more external threads, thereby allowing attachment to another instrument when the handle is coupled to the injection needle.

12. The injection needle of claim 11, wherein the elongate shaft includes a cannula opening at the second end, and wherein the cannula opening remains exposed when the handle is coupled to the injection needle to allow insertion of a device or an injectable material therein.

13. The injection needle of claim 10, wherein the one or more external threads are raised above the outer surface of the elongate shaft.

14. The injection needle of claim 13, wherein the drill adapter further comprises a cylindrical main body including one or more internal threads structured to engage with the one or more external threads at the tool attachment end, an elongate shank configured to extend away from the cylindrical main body in a direction opposite to the tip of the injection needle, and a bit portion extending from the elongate shank that is sized and shaped for engagement with a drill or power driver.

15. An injection needle configured to deliver material to a subchondral area of a bone joint to be treated, comprising:
a closed first end comprising a sharp, pointed tip sufficient to pierce bone tissue, a second end comprising a tool attachment end, and an elongate shaft extending therebetween and including a cylindrical outer surface defining an outer diameter, the shaft being partially cannulated and having one or more helical grooves near the first end that are recessed below the outer surface of the elongate shaft and that define a root diameter that is less than the outer diameter, the one or more helical grooves defining a grooved shaft section disposed between the first end and the second end, the needle further comprising one or more external threads located at the tool attachment end, one or more holes for ejection of an injectable material therethrough and disposed between and longitudinally spaced from the grooved shaft section and the tip, and a drill adapter, formed as a separate component and having a base portion structured for detachable engagement with the one or more external threads at the tool attachment end, the drill adapter further comprising an elongate shank configured to extend away from the base portion and including a bit portion sized and shaped for engagement with a drill or power driver.

* * * * *